US008334431B2

(12) United States Patent
Sampson et al.

(10) Patent No.: US 8,334,431 B2
(45) Date of Patent: Dec. 18, 2012

(54) AXMI-115, AXMI-113, AXMI-005, AXMI-163 AND AXMI-184: INSECTICIDAL PROTEINS AND METHODS FOR THEIR USE

(75) Inventors: Kimberly S. Sampson, Durham, NC (US); Daniel J. Tomso, Bahama, NC (US); Nadine Carozzi, Raleigh, NC (US); Tracy Hargiss, Chapel Hill, NC (US); Michael G. Koziel, Raleigh, NC (US); Nicholas B. Duck, Apex, NC (US); Shruti Agarwal, Durham, NC (US); Brian McNulty, Raleigh, NC (US); Chris Campbell, Cary, NC (US); Volker Heinrichs, Raleigh, NC (US)

(73) Assignee: Athenix Corporation, Morrisville, NC (US)

( * ) Notice: Subject to any disclaimer, the term of this patent is extended or adjusted under 35 U.S.C. 154(b) by 223 days.

(21) Appl. No.: 12/497,221

(22) Filed: Jul. 2, 2009

(65) Prior Publication Data

US 2010/0004176 A1    Jan. 7, 2010

Related U.S. Application Data

(60) Provisional application No. 61/077,812, filed on Jul. 2, 2008, provisional application No. 61/158,953, filed on Mar. 10, 2009.

(51) Int. Cl.
| *A01H 5/00* | (2006.01) |
| *A01H 5/10* | (2006.01) |
| *C12N 15/82* | (2006.01) |
| *C12N 15/32* | (2006.01) |
| *C07K 14/325* | (2006.01) |
| *A01N 37/18* | (2006.01) |

(52) U.S. Cl. ..... 800/302; 514/4.5; 536/23.71; 424/93.2; 800/279

(58) Field of Classification Search ..................... None
See application file for complete search history.

(56) References Cited

U.S. PATENT DOCUMENTS

| 6,570,005 B1 | 5/2003 | Schnepf et al. |
| 7,129,212 B2 | 10/2006 | Narva et al. |

FOREIGN PATENT DOCUMENTS

| EP | 1499176 | | 4/2010 |
| WO | WO 02/26995 A1 | | 4/2002 |
| WO | 03080656 A1 | | 10/2003 |
| WO | WO 03/080656 | * | 10/2003 |
| WO | WO 2008/039450 A2 | | 4/2008 |

OTHER PUBLICATIONS

Ziegler et al (1999, *Bacillus* Genetic Stock Center Catalog, part 2, p. 1-4 and 9).*

Liu J et al, "Identification of vip3A-type genes from *Bacillus thuringiensis* Strains and Characterization of a novel vip3A-type Gene"; Oct. 2007; pp. 432-438; Letters in Applied Microbiology, vol. 45, No. 4; XP002558332; ISSN: 0266-8254.

Estruch J J et al, "VIP3A, A Novel *Bacillus thuringiensis* Vegetative Insecticidal Protein with a Wide Spectrum of Activities Against Lepidopteran Insects", Proceedings of the National Academy of Sciences USA, vol. 93, May 1, 1996, pp. 5389-5394, XP002071759, ISSN: 0027-8424.

Lee M. K. et al, "The mode of action of the *Bacillus thuringiensis* Vegetative Insecticidal Protein Vip 3A Differs from that of Cry1Ab [delta]-endotoxin", Applied and Environmental Microbiology, American Society for Microbiology, US, vol. 69, No. 8, Aug. 1, 2003, pp. 4648-4657, XP002536190, ISSN: 0099-2240.

International Search Report and Written Opinion of the International Searching Authority for PCT/US2009/049527 mailed on Mar. 25, 2010.

NCBI Report for Accession No. CAI43275, Direct Submission Jan. 6, 2005.

NCBI Report for Accession No. ABH10614, direct submission Jun. 29, 2006.

EBI Report for Uniprot Accession No. 022547, Direct Submission Jan. 1, 1998.

EBI Report for Uniprot Accession No. A8JH48, Direct Submission Dec. 4, 2007.

Kindle, Karen L., "Amino-terminal and hydrophobic regions of the *Chlamydomonas reinhardtii* plastocyanin transit peptide are required for efficient protein accumulation in vivo," *Plant Molecular Biology*, 1998, vol. 38, pp. 365-377.

Leon, Rosa, et al., "Metabolic engineering of ketocarotenoids biosynthesis in the unicellular microalga *Chlamydomonas reinhardtii,*" *Journal of Biotechnology*, 2007, vol. 130, pp. 143-152.

Roesler, Keith R. and William L. Ogren, "Primary Structure of *Chlamydomonas reinhardtii* Ribulose 1,5-Bisphosphate Carboxylase/Oxygenase Activase and Evidence for a Single Polypeptide," *Plant Physiol.*, 1990, vol. 94, pp. 1837-1841.

Singh, Bijay, et al., "*Arabidopsis* Acetohydroxyacid Synthase Expressed in *Escherichia coli* is Insensitive to the Feedback Inhibitors," *Plant Physiol.*, 1992 vol. 99, pp. 812-816.

* cited by examiner

Primary Examiner — Anne Kubelik

(57) ABSTRACT

Compositions and methods for conferring insecticidal activity to host cells are provided. Compositions comprising a coding sequence for a delta-endotoxin polypeptide are provided. The coding sequences can be used in DNA constructs or expression cassettes for transformation and expression in host cells. Compositions also comprise transformed host cells. In particular, isolated delta-endotoxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:4, 5, 6, 13, or 14, or the nucleotide sequence set forth in SEQ ID NO:1, 2, 3, 11, or 12, as well as variants and fragments thereof.

16 Claims, 3 Drawing Sheets

```
Optaxmi113    MNMNNTKLSTRALPSFIDYFNGIYGFATGIKDIMNMIFKTDTGGDLTLDEILKNQQLLNE 60
Optaxmi005    MNMNNTKLNARALPSFIDYFNGIYGFATGIKDIMNMIFKTDTGGNLTLDEILKNQQLLNE 60
Optaxmi115    MNMNNTKLNARALPSFIDYFNGIYGFATGIKDIMNMIFKTDTGGDLTLDEILKNQQLLNE 60
              ********:*********************************:****************

Optaxmi113    ISGKLDGVNGSLNDLIAQGNLNTELSKEILKIANEQNQVLNDVNNKLDAINTMLHIYLPK 120
Optaxmi005    ISGKLDGVNGSLNDLIAQGNLNTELSKEILKIANEQNQVLNDVNNKLDAINTMLHIYLPK 120
Optaxmi115    ISGKLDGVNGSLNDLIAQGNLNTELSKEILKIANEQNQVLNDVNNKLDAINTMLNIYLPK 120
              ******************************************************:*****

Optaxmi113    ITSMLSDVMKQNYALSLQIEYLSKQLQEISDKLDIINVNVLINSTLTEITPAYQRIKYVN 180
Optaxmi005    ITSMLSDVMKQNYALSLQIEYLSKQLQEISDKLDIINVNVLINSTLTEITPAYQRIKYVN 180
Optaxmi115    ITSMLSDVMKQNYALSLQIEYLSRQLQEISDKLDVINLNVLINSTLTEITPSYQRIKYVN 180
              ***********************:**********:**:************:********

Optaxmi113    EKFEELTFATETNLKVKK-----DGSPADILDELTELTELAKSVTKNDVDGFEFYLNTFH 235
Optaxmi005    EKFEELTFATETTLKVKK-----DSSPADILDELTELTELAKSVTKNDVDGFEFYLNTFH 235
Optaxmi115    EKFDKLTFATESTLRAKQGIFNEDSFDNNTLENLTDLAELAKSITKNDVDSFEFYLHTFH 240
              ***::******::*:.*:     *.     : *::**:*:*****.*****.*****:***

Optaxmi113    DVMVGNNLFGRSALKTASELITKENVKTSGSEVGNVYNFLIVLTALQAKAFLTLTTCRKL 295
Optaxmi005    DVMVGNNLFGRSALKTASELIAKENVKTSGSEVGNVYNFLIVLTALQAKAFLTLTTCRKL 295
Optaxmi115    DVLIGNNLFGRSALKTASELITKDEIKTSGSEIGKVYSFLIVLTSLQAKAFLTLTTCRKL 300
              **::*****************::*:.:*****:*:**.******:***************

Optaxmi113    LGLADIDYTSIMNEHLNKEKEEFRVNILPTLSNTFSNPNYIKTKGSDEDAEVIIQAEPGH 355
Optaxmi005    LGLADIDYTSIMNEHLNKEKEEFRVNILPTLSNTFSNPNYAKVKGSDEDAKMIVEAKPGH 355
Optaxmi115    LGLSDIDYTSIMNEHLNNEKNEFRDNILPALSNKFSNPSYAKTIGSDNYAKVILESEPGY 360
              ***:*************:**:***:****:***.****.*  * ..***: *::::**:

Optaxmi113    ALVGFEMINDPSPALKVYQAKLTTNYQVDKQSLSETVYGDMDKILCPDKSQQMYYLHNIT 415
Optaxmi005    ALVGFEMSNDSITVLKVYEAKLKQNYQVDKDSLSEVIYGDMDKLLCPDQSEQIYYTNNIV 415
Optaxmi115    ALVGFEIINDPIPVLKAYKAKLKQNYQVDNQSLSEIVYLDIDKLFCPENSEQKYYTKNLT 420
              ******  **.  .**.*:***. :****::****::* *:**::**::*:*  **:..

Optaxmi113    FPNEYVITEIIFTKKKNSLRYEVIANYYEFSSGDIDLNKKLVKS--SEAEYSTLSVSND- 472
Optaxmi005    FPNEYVITKIDFTKKMKTLRYEVTANSYDSSTGEIDLNKKKVES--SEAEYRTLSAKDD- 472
Optaxmi115    FPDGYVITKITFEKKLNNLIYEATANFYDPSTGDIDLNKKQVESTFPQTDYITMDIGDDD 480
              **: ****.:*  ** :.* **.:**  *: *:******* *:*  .::::  *:.  :*

Optaxmi113    AIYMPLGVISETFLTPIKGFGLTVDESSRLVTLTCKSYLREILLATDLSNKATKLIVPPN 532
Optaxmi005    GVYMPLGVISETFLTPINGFGLQADENSRLITLTCKSYLRELLLATDLSNKETKLIVPPS 532
Optaxmi115    GIYMPLGVISETFLTPINSFGLEVDAKSKTLTLKCKSYLREYLLESDLKNKETGLIAPPN 540
              .:**************:.***  *  *: :**.*****.:. **:**.**:* **.**.

Optaxmi113    GFISNLVENGDIEADNIEPWKGNNKNAYVDHTGGVNGTKALYTQDDGEFSQFIGDKLKSK 592
Optaxmi005    GFISNIVENGNLEGENLEPWIANNKNAYVDHTGGVNGTRALYVHKDGGFSQFIGDKLKPK 592
Optaxmi115    VFISNVVKNWDIEEDSLEPWVANNKNAYVDNTGGIERSKALFTQGDGEFSQFIGDKLKPN 600
              ****:.:*  ::* :.:***.:********:***:  .:***.  .*.*********.:

Optaxmi113    TEYIIQYTVKGNTSIYLKDKKNENVIYEDKNNNLEAFQTITKRFTTELDSSDVYLVFKCK 652
Optaxmi005    TEYVIQYTVKGKPSIHLKNENTGYIHYEDTNNNLEDYQTITKRFTTGTDLKGVYLILKSQ 652
Optaxmi115    TDYIIQYTVKGKPAIYLKNKSTGYITYEDTNGNSEEFQTIAVKFTSETDLSQTHLVFKSQ 660
              *:*:*******:.:*:**:: ..  : ***.*.*. * *: :**::  *  .:*::* :
```

FIG. 1A

```
Optaxmi113   NGYKAWGDNFLITEIRPKE-VVSPELIKVENWIGMGGSNHVNPDSLLLFTGGRSILKQNL 711
Optaxmi005   NGDEAWGDNFTILEISPSEKLLSPELINVNNWIRTG-STHISGNTLTLYQGGGGNLKQNL 711
Optaxmi115   NGYEAWGDNFIILEAKLFETPESPELIKFNDWERFG-TTYITGNELRIDHSRGGYFRQSL 719
             ** :****** *  *    *   *****:.::*   * :.::. : * :  .  .::*.*

Optaxmi113   QLDSYSTYRVRFSLMVIGKAKVIIRNSS-EVLFEKSYVNDSEGVLEGVSETFTTKSIQDN 770
Optaxmi005   QLDSFSTYRVNFS--VTGDANVRIRNSR-EVLFEKRYMSG----AKDVSEIFTTKLGKDN 764
Optaxmi115   NIDSYSTYDLSFS-FSGLWAKVIVKNSRGVVLFEKVKNNGSS--YEDISESFTTASNKDG 776
             ::**:***  : **       *:* ::**   *****   ..    :.:** ***   :*.

Optaxmi113   FYVELSNEGTFGSKDVAYFYNFSIR---- 795
Optaxmi005   FYIELSQGNNLYGGPLVKFNDVSIK---- 789
Optaxmi115   FFIELTAER--TSSTFHSFRDISIKEKIE 803
             *::**:          .  . * :.**: ←
```

FIG. 1B

```
                           *        20         *        40         *        60         *        80
axmi-005 :        MNMNNTKLNARALPSFIDYFMGIYGFATGIKDIMNNIFKTDTGGNLTDEILKNQQLLNEISGKLDGVNGSLNDLIAQGMNLNTELSKEIL :  90
axmi-115 :        MNMNNTKLNARALPSFIDYFMGIYGFATGIKDIMNNIFKTDTGGDLTDEILKNQQLLNEISGKLDGVNGSLNDLIAQGMNLNTELSKEIL :  90

*       100         *       120         *       140         *       160         *       180
axmi-005 : KIANEQNQVLNDVNNKLDAINTHLHIYLPKITSHMLSDVHKQNYALSLQIEYLSKQLQEISDKLDIINVNVLINSTLTEITPAYQRIKYVN : 180
axmi-115 : KIANEQNQVLNDVNNKLDAINTHLNIYLPKITSHMLSDVHKQN

AXMI-115, AXMI-113, AXMI-005, AXMI-163 AND AXMI-184: INSECTICIDAL PROTEINS AND METHODS FOR THEIR USE

CROSS REFERENCE TO RELATED APPLICATION

This application claims the benefit of U.S. Provisional Application Ser. No. 61/077,812, filed Jul. 2, 2008, and U.S. Provisional Application Ser. No. 61/158,953, filed Mar. 10, 2009, the contents of which are hereby incorporated in their entirety by reference herein.

The official copy of the sequence listing is submitted concurrently with the specification as an ASCII formatted text file via EFS-Web, with a file name of "374397_SequenceListing.txt", a creation date of Jul. 1, 2009, and a size of 88 kilobytes. The sequence listing filed via EFS-Web is part of the specification and is hereby incorporated in its entirety by reference herein.

FIELD OF THE INVENTION

This invention relates to the field of molecular biology. Provided are novel genes that encode insecticidal proteins. These proteins and the nucleic acid sequences that encode them are useful in preparing insecticidal formulations and in the production of transgenic insect-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a "Greek key" configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Aside from delta-endotoxins, there are several other known classes of pesticidal protein toxins. The VIP1/VIP2 toxins (see, for example, U.S. Pat. No. 5,770,696) are binary pesticidal toxins that exhibit strong activity on insects by a mechanism believed to involve receptor-mediated endocytosis followed by cellular toxification, similar to the mode of action of other binary ("A/B") toxins. A/B toxins such as VIP, C2, CDT, CST, or the *B. anthracis* edema and lethal toxins initially interact with target cells via a specific, receptor-mediated binding of "B" components as monomers. These monomers then form homoheptamers. The "B" heptamer-receptor complex then acts as a docking platform that subsequently binds and allows the translocation of an enzymatic "A" component(s) into the cytosol via receptor-mediated endocytosis. Once inside the cell's cytosol, "A" components inhibit normal cell function by, for example, ADP-ribosylation of G-actin, or increasing intracellular levels of cyclic AMP (cAMP). See Barth et al. (2004) *Microbiol Mol Biol Rev* 68:373-402.

The intensive use of *B. thuringiensis*-based insecticides has already given rise to resistance in field populations of the diamondback moth, *Plutella xylostella* (Ferré and Van Rie (2002) *Annu. Rev. Entomol.* 47:501-533). The most common mechanism of resistance is the reduction of binding of the toxin to its specific midgut receptor(s). This may also confer cross-resistance to other toxins that share the same receptor (Ferré and Van Rie (2002)).

SUMMARY OF INVENTION

Compositions and methods for conferring insect resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in any of SEQ ID NO:4, 5, 6, 13, or 14, or a nucleotide sequence set forth in any of SEQ ID NO:1, 2, 3, 11, or 12, as well as variants and fragments thereof. Nucleotide sequences that are complementary to a nucleotide sequence of the invention, or that hybridize to a sequence of the invention are also encompassed.

The compositions and methods of the invention are useful for the production of organisms with insecticide resistance, specifically bacteria and plants. These organisms and compositions derived from them are desirable for agricultural purposes. The compositions of the invention are also useful for generating altered or improved delta-endotoxin proteins that have insecticidal activity, or for detecting the presence of delta-endotoxin proteins or nucleic acids in products or organisms.

The following embodiments are encompassed by the present invention:

1. An isolated nucleic acid molecule comprising a nucleotide sequence selected from the group consisting of:
   a) the nucleotide sequence of any of SEQ ID NO:1, 2, 3, 11, or 12, or a complement thereof;
   b) a nucleotide sequence that encodes a polypeptide comprising the amino acid sequence of any of SEQ ID NO:4, 5, 6, 13, or 14;
   c) a nucleotide sequence that encodes a polypeptide comprising an amino acid sequence having at least 96% sequence identity to the amino acid sequence of SEQ ID NO:4 or 14, wherein said amino acid sequence has insecticidal activity;
   d) a nucleotide sequence that encodes a polypeptide comprising an amino acid sequence having at least 95% sequence identity to the amino acid sequence of SEQ ID NO:6, wherein said amino acid sequence has insecticidal activity; and
   e) a nucleotide sequence encoding an insecticidal polypeptide that is a variant of SEQ ID NO:4, 5, 6, 13, or 14, wherein said variant is the result of one or more domain(s) of SEQ ID NO:4, 5, 6, 13, or 14 being exchanged with the corresponding domain(s) of SEQ ID NO:4, 5, 6, 13, or 14, wherein said nucleotide sequence encodes an insecticidal polypeptide.

2. The isolated nucleic acid molecule of embodiment 1, wherein said nucleotide sequence is a synthetic sequence that has been designed for expression in a plant.

3. The isolated nucleic acid molecule of embodiment 2, wherein said nucleotide sequence is selected from the group consisting of SEQ ID NO:15, 16, 17, and 18.

4. An expression cassette comprising the nucleic acid molecule of embodiment 1.

5. The expression cassette of embodiment 4, further comprising a nucleic acid molecule encoding a heterologous polypeptide.

6. A host cell that contains the expression cassette of embodiment 4.

7. The host cell of embodiment 6 that is a bacterial host cell.

8. The host cell of embodiment 6 that is a plant cell.

9. A transgenic plant comprising the host cell of embodiment 8.

10. The transgenic plant of embodiment 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. An isolated polypeptide with insecticidal activity, selected from the group consisting of:
   a) a polypeptide comprising the amino acid sequence of any of SEQ ID NO:4, 5, 6, 13, or 14;
   b) a polypeptide comprising an amino acid sequence having at least 96% sequence identity to the amino acid sequence of SEQ ID NO:4 or 14, wherein said amino acid sequence has insecticidal activity;
   c) a polypeptide comprising an amino acid sequence having at least 95% sequence identity to the amino acid sequence of SEQ ID NO:6, wherein said amino acid sequence has insecticidal activity;
   d) a polypeptide that is encoded by the nucleotide sequence of any of SEQ ID NO:1, 2, 3, 11, or 12; and
   e) a polypeptide that is a variant of SEQ ID NO:4, 5, 6, 13, or 14, wherein said variant is the result of one or more domain(s) of SEQ ID NO:4, 5, 6, 13, or 14 being exchanged with the corresponding domain(s) of SEQ ID NO:4, 5, 6, 13, or 14, wherein said polypeptide has insecticidal activity.

12. The polypeptide of embodiment 11 further comprising heterologous amino acid sequences.

13. An antibody that selectively binds to the polypeptide of embodiment 11.

14. A composition comprising the polypeptide of embodiment 11.

15. The composition of embodiment 14, wherein said composition is selected from the group consisting of a powder, dust, pellet, granule, spray, emulsion, colloid, and solution.

16. The composition of embodiment 14, wherein said composition is prepared by desiccation, lyophilization, homogenization, extraction, filtration, centrifugation, sedimentation, or concentration of a culture of *Bacillus thuringiensis* cells.

17. The composition of embodiment 14, comprising from about 1% to about 99% by weight of said polypeptide.

18. A method for controlling a lepidopteran or coleopteran pest population comprising contacting said population with an insecticidally-effective amount of the polypeptide of embodiment 11.

19. A method for killing a lepidopteran or coleopteran pest, comprising contacting said pest with, or feeding to said pest, an insecticidally-effective amount of the polypeptide of embodiment 11.

20. A method for producing a polypeptide with insecticidal activity, comprising culturing the host cell of embodiment 6 under conditions in which the nucleic acid molecule encoding the polypeptide is expressed.

21. A plant having stably incorporated into its genome a DNA construct comprising a nucleotide sequence that encodes a protein having insecticidal activity, wherein said nucleotide sequence is selected from the group consisting of:
   a) the nucleotide sequence of any of SEQ ID NO:1, 2, 3, 11, or 12;
   b) a nucleotide sequence that encodes a polypeptide comprising the amino acid sequence of any of SEQ ID NO:4, 5, 6, 13, or 14;
   c) a nucleotide sequence that encodes a polypeptide comprising an amino acid sequence having at least 96% sequence identity to the amino acid sequence of SEQ ID NO:4 or 14, wherein said amino acid sequence has insecticidal activity;
   d) a nucleotide sequence that encodes a polypeptide comprising an amino acid sequence having at least 95% sequence identity to the amino acid sequence of SEQ ID NO:6, wherein said amino acid sequence has insecticidal activity; and e) a nucleotide sequence encoding an insecticidal polypeptide that is a variant of SEQ ID NO:4, 5, 6, 13, or 14, wherein said variant is the result of one or more domain(s) of SEQ ID NO:4, 5, 6, 13, or 14 being exchanged with the corresponding domain(s) of SEQ ID NO:4, 5, 6, 13, or 14, wherein said nucleotide sequence encodes an insecticidal polypeptide;

wherein said nucleotide sequence is operably linked to a promoter that drives expression of a coding sequence in a plant cell.

22. The plant of embodiment 21, wherein said plant is a plant cell.

23. A transgenic seed of the plant of embodiment 21, wherein said seed comprises a nucleotide sequence selected from the group consisting of:

a) the nucleotide sequence of any of SEQ ID NO:1, 2, 3, 11, or 12;

b) a nucleotide sequence that encodes a polypeptide comprising the amino acid sequence of any of SEQ ID NO:4, 5, 6, 13, or 14;

c) a nucleotide sequence that encodes a polypeptide comprising an amino acid sequence having at least 96% sequence identity to the amino acid sequence of SEQ ID NO:4 or 14, wherein said amino acid sequence has insecticidal activity;

d) a nucleotide sequence that encodes a polypeptide comprising an amino acid sequence having at least 95% sequence identity to the amino acid sequence of SEQ ID NO:6, wherein said amino acid sequence has insecticidal activity; and e) a nucleotide sequence encoding an insecticidal polypeptide that is a variant of SEQ ID NO:4, 5, 6, 13, or 14, wherein said variant is the result of one or more domain(s) of SEQ ID NO:4, 5, 6, 13, or 14 being exchanged with the corresponding domain(s) of SEQ ID NO:4, 5, 6, 13, or 14, wherein said nucleotide sequence encodes an insecticidal polypeptide.

24. A method for protecting a plant from an insect pest, comprising introducing into said plant or cell thereof at least one expression vector comprising a nucleotide sequence that encodes an insecticidal polypeptide, wherein said nucleotide sequence is selected from the group consisting of:

a) the nucleotide sequence of any of SEQ ID NO:1, 2, 3, 11, or 12;

b) a nucleotide sequence that encodes a polypeptide comprising the amino acid sequence of any of SEQ ID NO:4, 5, 6, 13, or 14;

c) a nucleotide sequence that encodes a polypeptide comprising an amino acid sequence having at least 96% sequence identity to the amino acid sequence of SEQ ID NO:4 or 14, wherein said amino acid sequence has insecticidal activity;

d) a nucleotide sequence that encodes a polypeptide comprising an amino acid sequence having at least 95% sequence identity to the amino acid sequence of SEQ ID NO:6, wherein said amino acid sequence has insecticidal activity; and e) a nucleotide sequence encoding an insecticidal polypeptide that is a variant of SEQ ID NO:4, 5, 6, 13, or 14, wherein said variant is the result of one or more domain(s) of SEQ ID NO:4, 5, 6, 13, or 14 being exchanged with the corresponding domain(s) of SEQ ID NO:4, 5, 6, 13, or 14, wherein said nucleotide sequence encodes an insecticidal polypeptide.

25. The method of embodiment 24, wherein said plant produces an insecticidal polypeptide having insecticidal activity against a lepidopteran or coleopteran pest.

BRIEF DESCRIPTION OF THE FIGURES

FIGS. 1A and 1B show an alignment of AXMI-113 (SEQ ID NO:5), AXMI-005 (SEQ ID NO:4), and AXMI-115 (SEQ ID NO:6). The left and right arrows mark the boundaries of the C-terminal $\frac{1}{3}^{rd}$ region of the proteins.

FIG. 2 depicts domains within AXMI-005 and AXMI-115 that are swapped to generate new toxins.

DETAILED DESCRIPTION

The present invention is drawn to compositions and methods for regulating insect resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess insecticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered insecticidal proteins by methods known in the art, such as domain swapping or DNA shuffling. See, for example, Table 2 and FIG. 2. The proteins find use in controlling or killing lepidopteran, coleopteran, and other insect populations, and for producing compositions with insecticidal activity.

By "delta-endotoxin" is intended a toxin from *Bacillus thuringiensis* that has toxic activity against one or more pests, including, but not limited to, members of the Lepidoptera, Diptera, and Coleoptera orders, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having insecticidal activity. Processing may occur in the organism the protein is expressed in, or in the pest after ingestion of the protein.

Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Provided herein are novel isolated nucleotide sequences that confer insecticidal activity. Also provided are the amino acid sequences of the delta-endotoxin proteins. The protein resulting from translation of this gene allows cells to control or kill insects that ingest it.

Isolated Nucleic Acid Molecules, and Variants and Fragments Thereof

One aspect of the invention pertains to isolated or recombinant nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1, 2, 3, 11, or 12, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:4, 5, 6, 13, or 14.

Nucleic acid molecules that are fragments of these delta-endotoxin encoding nucleotide sequences are also encompassed by the present invention. By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length delta-endotoxin encoding nucleotide sequence disclosed herein depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain insecticidal activity. By "retains activity" is intended that the fragment will have at least about 30%, at least about 50%, at least about 70%, 80%, 90%, 95% or higher of the insecticidal activity of the delta-endotoxin protein. Methods for measuring insecticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length delta-endotoxin protein of the invention.

Preferred delta-endotoxin proteins of the present invention are encoded by a nucleotide sequence sufficiently identical to the nucleotide sequence of SEQ ID NO:1, 2, 3, 11, or 12. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of one of SEQ ID NO:1, 2, 3, 11, or 12, or across the entirety of one of SEQ ID NO:4, 5, 6, 13, or 14). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM 120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining insecticidal activity. By "retains activity" is intended that the variant will have at least about 30%, at least about 50%, at least about 70%, or at least about 80% of the insecticidal activity of the native protein. Methods for measuring insecticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known delta-endotoxin sequences. Examples of residues that are conserved but that may allow conservative amino acid substitutions and still retain activity include, for example, residues that have only conservative substitutions between all proteins contained in an alignment of the amino acid sequences of the present invention and known delta-endotoxin sequences. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in depending upon circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof Delta-endotoxin proteins are also encompassed within the present invention. By "delta-endotoxin protein" is intended a protein having the amino acid sequence set forth in SEQ ID NO:4, 5, 6, 13, or 14. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in any of SEQ ID NO:4, 5, 6, 13, or 14 and that exhibit insecticidal activity. A biologically active portion of a delta-endotoxin protein can be a polypeptide that is, for example, 10, 25, 50, 100 or more amino acids in length. Such biologically active portions can be prepared by recombinant techniques and evaluated for insecticidal activity. Methods for measuring insecticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:4, 5, 6, 13, or 14. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, 1100, 1150, 1200, 1250, or 1300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:4, 5, 6, 13, or 14. Variants also include polypeptides encoded by a nucleic acid molecule that hybridizes to the nucleic acid molecule of SEQ ID NO:1, 2, 3, 11, or 12, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining insecticidal activity. Methods for measuring insecticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode insecticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions of one or more amino acids of SEQ ID NO:4, 5, 6, 13, or 14, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired insecticidal activity. However, it is understood that the ability of a delta-endotoxin to confer insecticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with insecticidal activity, for example by performing an assay to test for insecticidal activity. Generally, the protein is mixed and used in feeding assays. See, for example Marrone et al. (1985) *J. of Economic Entomology* 78:290-293. Such assays can include contacting plants with one or more insects and determining the plant's ability to survive and/or cause the death of the insects. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved insecticidal activity or target spectrum. Methods for generating recombinant proteins and testing them for insecticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native, or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, resolved in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Insecticidal Activity in Plants

In another aspect of the invention, one may generate transgenic plants expressing a delta-endotoxin that has insecticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for insecticidal activity.

Fertile plants expressing a delta-endotoxin may be tested for insecticidal activity, and the plants showing optimal activity selected for further breeding. Methods are available in the art to assay for insect activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, Brassica sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Insect Control

General methods for employing strains comprising a nucleotide sequence of the present invention, or a variant thereof, in insect control or in engineering other organisms as insecticidal agents are known in the art. See, for example U.S. Pat. No. 5,039,523 and EP 0480762A2.

The Bacillus strains containing a nucleotide sequence of the present invention, or a variant thereof, or the microorganisms that have been genetically altered to contain an insecticidal gene and protein may be used for protecting agricultural crops and products from insects. In one aspect of the invention, whole, i.e., unlysed, cells of a toxin (insecticide)-producing organism are treated with reagents that prolong the activity of the toxin produced in the cell when the cell is applied to the environment of target insect(s).

Alternatively, the insecticide is produced by introducing a delta-endotoxin gene into a cellular host. Expression of the delta-endotoxin gene results, directly or indirectly, in the intracellular production and maintenance of the insecticide. In one aspect of this invention, these cells are then treated under conditions that prolong the activity of the toxin produced in the cell when the cell is applied to the environment of target insect(s). The resulting product retains the toxicity of the toxin. These naturally encapsulated insecticides may then be formulated in accordance with conventional techniques for application to the environment hosting a target insect, e.g., soil, water, and foliage of plants. See, for example EPA 0192319, and the references cited therein. Alternatively, one may formulate the cells expressing a gene of this invention such as to allow application of the resulting material as an insecticide.

Insecticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, insecticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the insecticidal formulation.

Methods of applying an active ingredient of the present invention or an agrochemical composition of the present invention that contains at least one of the insecticidal proteins produced by the bacterial strains of the present invention include leaf application, seed coating and soil application. The number of applications and the rate of application depend on the intensity of infestation by the corresponding insect.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such insecticidal polypeptide, the polypeptide may be present in a concentration of from about 1% to about 99% by weight.

Lepidopteran, coleopteran, or other insects may be killed or reduced in numbers in a given area by the methods of the invention, or may be prophylactically applied to an environmental area to prevent infestation by a susceptible insect. Preferably the insect ingests, or is contacted with, an insecticidally-effective amount of the polypeptide. By "insecticidally-effective amount" is intended an amount of the insecticide that is able to bring about death to at least one insect, or to noticeably reduce insect growth, feeding, or normal physiological development. This amount will vary depending on such factors as, for example, the specific target insects to be controlled, the specific environment, location, plant, crop, or agricultural site to be treated, the environmental conditions, and the method, rate, concentration, stability, and quantity of application of the insecticidally-effective polypeptide composition. The formulations may also vary with respect to climatic conditions, environmental considerations, and/or frequency of application and/or severity of insect infestation.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachimidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, Crambidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus* leucopterus, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca*

*fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise introducing into a plant or plant cell a polynucleotide comprising an insecticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the insecticidal sequence.

In specific methods, plant yield is increased as a result of improved insect resistance of a plant expressing an insecticidal protein disclosed herein. Expression of the insecticidal protein results in a reduced ability of an insect to infest or feed on the plant, thus improving plant yield.

The following examples are offered by way of illustration and not by way of limitation.

EXPERIMENTAL

Example 1

Discovery of a Novel Toxin Gene Axmi115 from the *Bacillus thuringiensis* Strain ATX12983

The complete gene sequence was identified from the selected strain via the MiDAS genomics approach as follows:

- Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.
- Mechanical or enzymatic shearing of the extrachromosomal DNA to generate size-distributed fragments.
- Sequencing of the fragmented DNA
- Identification of putative toxin genes via homology and/or other computational analyses.
- When required, sequence finishing of the gene of interest by one of several PCR or cloning strategies (e.g. TAIL-PCR).

The novel gene is referred to herein as axmi-115 (SEQ ID NO:3), and the encoded amino acid referred to as AXMI-115 (SEQ ID NO:6). Synthetic nucleotide sequences encoding AXMI-115 is set forth in SEQ ID NO:15 and 16.

Gene and Protein Characteristics

Gene length, DNA base pairs: 2409

Protein length, amino acid residues: 803

Estimated protein molecular weight, Da: 90877

Known homologs and approximate percent identity:

Vip3Af1-70.7%

Axmi005-70.4%

Axmi026-70.4%

Vip3Aa7-70.1

Example 2

Novel Insecticidal Protein AXMI-005 from the *Bacillus Thuringiensis* Strain ATX13002

The AXMI-005 insecticidal gene was identified from the strain ATX13002 using the MiDAS approach as described in U.S. Patent Publication No. 20040014091, which is herein incorporated by reference in its entirety, using the following steps:

Steps taken in the current strategy to gene discovery:

Step 1: Culture from the strain was grown in large quantities. The plasmid DNA was then separated from the chromosomal DNA by a cesium chloride gradient spun in an ultracentrifuge. The purified plasmid DNA was then nebulized to a 5-10 kb size range appropriate for coverage of an average sized coding region. The fragment ends were polished then ligated overnight into a vector cut with a restriction enzyme producing blunt ends.

Step 3: Once the shotgun library quality was checked and confirmed, colonies were grown, prepped and sequenced in a 96-well format. The library plates were end sequenced off of the vector backbone for initial screening.

Step 5: All of the reads were compiled into an assembly project and aligned together to form contigs. These contigs, along with any individual read that may not have been added to a contig, were analyzed using BLAST, using a batch format, against an internal database made up of all classes of known delta-endotoxin genes. Any contigs or individual reads that pulled up any homology to a known gene were analyzed further by selecting a single clone from the library that covered the entire hypothesized coding region.

Step 6: The individual clone covering the area of interest was then walked over read by read by designing primers to extend the sequence. This was done until both end reads of the clone were joined and the coverage was at least 2×. The completed contig of the single clone was then analyzed using BLAST (both blastn and blastx) against a public database of all known insecticidal genes. Hits from both searches were then pulled from an internal database of all the genes (clipped to coding sequence only) and aligned with the completed library clone sequence to determine the percentage of divergence from the known gene.

A novel gene, referred to herein as axmi-005 (SEQ ID NO:1), and the encoded amino acid referred to as AXMI-005 (SEQ ID NO:4) were identified by this approach. Searching of public sequence databases, including the GENBANK® databases, showed that AXMI-005 is a unique protein that has highest homology (94.9%) to the vip3Aa insecticidal protein (GenePept ID L48841).

A synthetic sequence encoding the AXMI-005 protein was designed and termed optaxmi-005. The nucleotide sequence is set forth in SEQ ID NO:7 and encodes the amino acid sequence set forth in SEQ ID NO:9 (with the addition of a C-terminal histidine tag). The optaxmi-005 gene disclosed herein can be used with or without the C-terminal histidine tag.

Example 3

Discovery of a Novel Toxin Gene Axmi-113 from the *Bacillus thuringiensis* Strain ATX12987

The complete gene sequence was identified from the selected strain via the MiDAS genomics approach as follows:
  Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.
  Mechanical or enzymatic shearing of the extrachromosomal DNA to generate size-distributed fragments.
  Sequencing of the fragmented DNA
  Identification of putative toxin genes via homology and/or other computational analyses.
  When required, sequence finishing of the gene of interest by one of several PCR or cloning strategies (e.g. TAIL-PCR).

The novel gene is referred to herein as axmi-113 (SEQ ID NO:2), and the encoded amino acid referred to as AXMI-113 (SEQ ID NO:5).
Gene and Protein Characteristics
Gene length, DNA base pairs: 2385
Protein length, amino acid residues: 795
Estimated protein molecular weight, Da: 89475
Known homologs and approximate percent identity:
  Vip3Ah-99%
  Vip3Aa18-79.8%
  Axmi005-79%

A synthetic sequence encoding the AXMI-113 protein was designed and termed optaxmi-113. The nucleotide sequence is set forth in SEQ ID NO:8 and encodes the amino acid sequence set forth in SEQ ID NO:5 or 10 (with the addition of a C-terminal histidine tag). The optaxmi-113 gene disclosed herein can be used with or without the C-terminal histidine tag.

Example 4

Discovery of Novel Toxin Genes Axmi-163 and Axmi-184 from the *Bacillus thuringiensis* Strain ATX14775

The complete gene sequence for each was identified from the selected strain via the MiDAS genomics approach as follows:
  Preparation of Extrachromosomal DNA from the Strain. Extrachromosomal DNA contains a mixture of some or all of the following: plasmids of various size; phage chromosomes; genomic DNA fragments not separated by the purification protocol; other uncharacterized extrachromosomal molecules.
  Mechanical or enzymatic shearing of the extrachromosomal DNA to generate size-distributed fragments.
  Sequencing of the fragmented DNA
  Identification of putative toxin genes via homology and/or other computational analyses.
  When required, sequence finishing of the gene of interest by one of several PCR or cloning strategies (e.g. TAIL-PCR).

The novel gene referred to herein as axmi-163 is set forth in SEQ ID NO:11, and the encoded amino acid referred to as AXMI-163 is set forth in SEQ ID NO:13.
Gene and Protein Characteristics
Gene length, DNA base pairs: 2370
Protein length, amino acid residues: 790
Estimated protein molecular weight, Da: 88,700
Known homologs and approximate percent identity:
  SEQ ID NO:17 from U.S. Pat. No. 7,129,212-98%
  Axmi005-78%

The novel gene referred to herein as axmi-184 is set forth in SEQ ID NO:12, and the encoded amino acid referred to as AXMI-184 is set forth in SEQ ID NO:14. Synthetic nucleotide sequences encoding AXMI-184 are set forth in SEQ ID NO:17 and 18.
Gene and Protein Characteristics
Gene length, DNA base pairs: 2370
Protein length, amino acid residues: 790
Estimated protein molecular weight, Da: 88,300
Known homologs and approximate percent identity:
  Vip3Af1-93%
  Axmi005-86%

Example 5

Construction of Synthetic Sequences

In one aspect of the invention, synthetic axmi sequences are generated. These synthetic sequences have an altered DNA sequence relative to the parent axmi sequence, and encode a protein that is collinear with the parent AXMI protein to which it corresponds, but lacks the C-terminal "crystal domain" present in many delta-endotoxin proteins.

In another aspect of the invention, modified versions of synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (Genebank ID GI:14276838; Miller et al. (2001) Plant Physiology 127: 594-606) is known in the art to result in endoplasmic reticulum targeting of heterologous proteins. If the resulting fusion protein also contains an endoplasmic retention sequence comprising the peptide N-terminus-lysine-aspartic acid-glutamic acid-leucine (i.e. the "KDEL" motif (SEQ ID NO:19) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Example 6

Expression in *Bacillus*

As an example of the expression of the genes and proteins of the invention in *Bacillus* species, the insecticidal gene disclosed herein is amplified by PCR, and the PCR product is cloned into the *Bacillus* expression vector pAX916, or another suitable vector, by methods well known in the art. The resulting *Bacillus* strain, containing the vector with axmi gene is cultured on a conventional growth media, such as CYS media (10 g/l Bacto-casitone; 3 g/l yeast extract; 6 g/l KH$_2$PO$_4$; 14 g/l K$_2$HPO$_4$; 0.5 mM MgSO$_4$; 0.05 mM MnCl$_2$; 0.05 mM FeSO$_4$), until sporulation is evident by microscopic examination. Samples are prepared and tested for activity in bioassays.

Example 7

Expression in E. coli

As an example of a method of expression of the genes and proteins of the invention in *E. coli* based systems, the complete ORF of each axmi gene is cloned into an *E. coli* expression vector based on pRSF1b. The resulting clones are confirmed by restriction analysis and finally, by complete sequencing of the cloned gene.

For expression in *E. coli*, BL21*DE3 is transformed with the vector expressing the axmi gene. Single colonies are inoculated in LB supplemented with kanamycin and grown overnight at 37° C. The following day, fresh medium is inoculated in duplicate with 1% of overnight culture and grown at 37° C. to logarithmic phase. Subsequently, cultures are induced with 1 mM isopropyl β-D-1-thiogalactopyranoside (IPTG) for 3 hours at 37° C. or overnight at 20° C. Each cell pellet is suspended in 50 mM sodium carbonate buffer, pH 10.5 supplemented with 1 mM DTT dithiothreitol and sonicated. Samples are prepared and tested for activity in bioassays.

Example 8

Expression of AXMI-115, AXMI-113, and AXMI-005 in *E. coli*

*E. coli* clones were generated that contained DNA segments containing the complete open reading frame as well as a portion of the DNA region naturally occurring upstream and adjacent to each gene. This DNA segment for each of axmi-113 (SEQ ID:2), axmi-115 (SEQ ID NO:3) or axmi-005 (SEQ ID NO:1) was amplified and cloned into the vector pAX916, to yield the clones pAX5463, pAX5464 and pAX5465 respectively. The resulting clones were confirmed by restriction analysis and by complete sequencing of the cloned fragments.

*E. coli* cells were transformed with each of the clones pAX5463, pAX5464 and pAX5465.

axmi005, axmi113 and axmi115 genes that had their codons optimized for expression in corn, and had a C-terminal his6-tag added, were also expressed from *E. coli* expression vector utilizing T7 promoter. In addition, constructs were also generated that expressed N-terminal his6-tagged or untagged versions of optaxmi005 (pAX5475, pAX5478) and optaxmi115 (pAX5476, pAX5477).

Single *E. coli* colonies of the axmi-115, axmi-113, and axmi-005 expressing clones were then grown overnight at 37° C. in LB medium. The following day, fresh medium was inoculated in duplicate with 1% of overnight culture and grown at 37° C. to logarithmic phase. Subsequently, cultures were induced with 1 mM IPTG overnight at 20° C. The resulting cells were collected by centrifugation, and suspended in either 50 mM sodium carbonate buffer, pH 10.5 supplemented with 1 mM DTT or 50 mM Tris Cl buffer, pH 8 with 1 mM DTT prior to sonication. SDS-PAGE analysis showed expression of a ~90 kD protein in all samples.

Example 9

Insect Bioassays of *E. coli* Expressed Proteins

Soluble extracts containing AXMI-005, AXMI-113, or AXMI-115 were tested in insect assays with appropriate controls. Twenty four well tissue culture plates (Corning) were filled with 1 ml of multi-species diet (Bio-Serv) and allowed to solidify. Once solidified, 40 μl of protein sample was placed on the diet surface of each well and allowed to soak in/dry at room temperature. Depending upon the experiment, either egg masses or neonate larvae were placed in each well. Plates were sealed with gas-permeable membranes (Research Products International) and incubated at 25° C. and 90% relative humidity. After five or seven days, samples were scored visually compared to a buffer only or non-transformed extract control.

Strong activity of AXMI-005 extracts was observed on *Helicoverpa zea* (HZ), *Heliothis virescens* (HV), Fall Armyworm (FAW), Black cutworm (BCW), Sugarcane borer (SCB), and Velvet Bean caterpillar (VBC). AXMI-005 also showed activity on Southwestern Corn Borer (SWCB).

Strong activity of AXMI-115 extracts was observed on *Heliothis virescens*, Fall Armyworm, Black cutworm, and Velvet Bean caterpillar. AXMI-115 also exhibited activity on the European Corn Borer (ECB), SCB, SWCB, and Diamondback moth (DBM). Activity of AXMI-115 on *Helicoverpa zea* (HZ) was less pronounced than for the other insects tested, but was still significant.

Activity of each of the AXMI-005 and AXMI-115 extracts was scored, and assigned a number from 1 to 5 based on relative activity in the assays. A summary of the scores in a particular assay is shown in Table 1.

AXMI-005 showed some activity on SWCB (score of 2) and high levels of activity on Hz, Hv, FAW, BCW and VBC (scores of 4 to 5). AXMI-115 showed high levels of activity on SWCB (80% mortality), ECB, FAW and VBC (scores of 4 to 5) and lesser activity on Hz and Hv. AXMI-113 also showed high activity on SWCB (score of 4 with 20% mortality) and on SCB. No activity was seen on the other insects tested.

TABLE 1

Insecticidal activity of AXMI-115, AXMI-113, and AXMI-005*

| | Axmi115 (pH 10.5) | Axmi115 (pH 8) | Axmi005 (pH 10.5) | Axmi005 (pH 8) | Axmi113 (pH 10.5) |
|---|---|---|---|---|---|
| Hz | 0 | 0 | 4 | 4 | 0 |
| ECB live infest | 2 | 4 | 0 | 0 | 0 |
| Hv | 0 | 0 | 4 | 4/5 | 0 |
| FAW | 4 | 2 | 4/5 | 4/5 | 0 |
| BCW | 0 | 0 | 3/4 | 4 | 0 |
| VBC | 4 | 3 | 4 | 4/5 | 0 |
| SWCB | 4; 80% mortality | 3; 50% mortality | 2 | ND | 4; 20% mortality |
| SCB | ND | 3; 25% mortality | ND | 4; 100% mortality | 3; 50% mortality |
| DBM | ND | 2/3 | 0 | 0 | 0 |

*= represented as stunt and mortality percent where stunting is scored according to the following scale:

| Score | Definition |
|---|---|
| 0 | No Activity |
| 1 | Slight, non-uniform stunt |
| 2 | Non-uniform stunt |
| 3 | Uniform stunt |
| 4 | Uniform stunt with mortality (expressed as a percentage) |
| 5 | Uniform stunt with 100% mortality |

Example 10

Bioassay of Axmi 184

Gene Expression and Purification

The DNA region encoding the toxin domain of Axmi 184 was cloned into an E. coli expression vector pMAL-C4x behind the malE gene coding for Maltose binding protein (MBP). This in-frame fusion resulted in MBP-Axmi084 fusion protein expression in E. coli.

For expression in E. coli, BL21*DE3 was transformed with individual plasmids. Single colony was inoculated in LB supplemented with carbenicillin and glucose, and grown overnight at 37° C. The following day, fresh medium was inoculated with 1% of overnight culture and grown at 37° C. to logarithmic phase. Subsequently, cultures were induced with 0.3 mM IPTG for overnight at 20° C. Each cell pellet was suspended in 20 mM Tris-Cl buffer, pH 7.4+200 mM NaCl+1 mM DTT+protease inhibitors and sonicated. Analysis by SDS-PAGE confirmed expression of fusion proteins.

Total cell free extracts were run over amylose column attached to FPLC for affinity purification of MBP-AXMI 184 fusion proteins. Bound fusion protein was eluted from the resin with 10 mM maltose solution. Purified fusion proteins were then cleaved with either Factor Xa or trypsin to remove the amino terminal MBP tag from the AXMI 184 protein. Cleavage and solubility of the proteins was determined by SDS-PAGE.

Cleaved proteins were tested in insect assays with appropriate controls. A 5-day read of the plates showed following activities of AXMI-184 against Diamondback moth.

Example 11

Domain Swapping axmi005, axmi113 and axmi115 genes that had their codons optimized for expression in corn were used in this example. Plasmids expressing untagged versions of optaxmi005 (pAX5478), optaxmi113 (pAX5493) and optaxmi115 (pAX5477) were used to design DNA swap constructs as describe here.

AXMI-005, AXMI-113 and AXMI-115 have significant sequence identity/similarity in their N-terminal 2/3$^{rd}$ region. The remaining 1/3$^{rd}$ region in their C-termini (CT) shows substantial sequence divergence as seen in the protein sequence alignment provided as FIGS. 1A and 1B.

The protein region of AXMI-113 between the forward and reverse arrows shown in FIG. 1 was replaced with the corresponding fragment of either AXMI-005 (to give pAX5492) or AXMI-115 (pAX5494).

For expression in E. coli, BL21*DE3 was transformed with individual constructs. A single colony was inoculated in LB supplemented with kanamycin and grown overnight at 37° C. The following day, fresh medium was inoculated in duplicate with 1% of overnight culture and grown at 37° C. to logarithmic phase. Subsequently, cultures were induced with 1 mM IPTG overnight at 20° C. Cell pellet was suspended in 50 mM sodium carbonate buffer, pH 10.5 supplemented with 1 mM DTT, and sonicated. Analysis by SDS-PAGE showed extremely good soluble expression of all proteins.

Filter sterilized, soluble extracts expressing OptAxmi005, 113, 115, Optaxmi113+CT of Optaxmi005 and Optaxmi113+CT of Optaxmi115 were tested in insect assays with appropriate controls. As shown in Example 9, AXMI-113 showed high activity on SWCB (25% mortality). It showed an additional activity on SCB (50% mortality).

Also as shown in Example 9, AXMI-005 showed activity on SWCB, Hz, Hv, FAW, BCW and VBC. It showed an additional activity on SCB (25% mortality). AXMI-115 was also found to have some activity on SCB.

The fusion of AXMI-113+CT of AXMI-005 showed all of the insect activities seen with AXMI-005. In other words, replacement of the C-terminal fragment of AXMI-113 with that of AXMI-005 bestowed upon it the insect activities that were otherwise missing in its naturally occurring form.

Additional toxin protein sequences can be generated by swapping domains from one protein into another. For example, one or more of the AXMI-005 domains shown in FIG. 2 are introduced into AXMI-115. The domains are introduced using the sense ("s") and antisense ("a") oligonucleotides shown in Table 2. The portion of the axmi-005 sequence that is being introduced into the axmi-115 sequence is shown in bold print. The flanking sequences in each oligonucleotide are axmi-115 sequences that are used for annealing the oligonucleotides to the axmi-115 template. The number following the term "sub" in each primer name corresponds to the numbered boxes in FIG. 2. Similar oligonucleotides can be designed to swap domains between multiple sequences, for example, between the AXMI-005, AXMI-113, AXMI-115, AXMI-163 and AXMI-184 sequences described herein.

TABLE 2

| Oligo-<br>nucleotide<br>primer | Sequence | SEQ<br>ID<br>NO: |
|---|---|---|
| axmi115sub1 s | AAC ACC GGC GGC GTC AAT GGA ACA<br>AGG GCG CTC TTC ACC CA | 20 |
| axmi115sub1 a | TGG GTG AAG AGC GCC CTT GTT CCA<br>TTG ACG CCG CCG GTG TT | 21 |
| axmi115sub10 s | GCC CGG AGC TCA TCA ATG TCA ACA<br>ACT GGA TCA GAA CTG GCA CCA CCT<br>ACA TCA C | 22 |
| axmi115sub10 a | GTG ATG TAG GTG GTG CCA GTT CTG<br>ATC CAG TTG TTG ACA TTG ATG AGC<br>TCC GGG C | 23 |
| axmi115sub11 s | ATG ATT GGG AGA GGT TCG GAA GCA<br>CCC ACA TCA GCG GCA ATG AGC TGA<br>GG | 24 |
| axmi115sub11 a | CCT CAG CTC ATT GCC GCT GAT GTG<br>GGT GCT TCC GAA CCT CTC CCA ATC<br>AT | 25 |
| axmi115sub12 s | CTA CAT CAC CGG CAA TAC CTT GAC<br>GCT CTA CCA AGG AGG AGG AGG CTA<br>CTT CCG C | 26 |
| axmi115sub12 a | GCG GAA GTA GCC TCC TCC TCC TTG<br>GTA GAG CGT CAA GGT ATT GCC GGT<br>GAT GTA G | 27 |
| axmi115sub14 s | CGA CAG CTA CAG CAC CTA CAG GGT<br>GAA CTT CTC CGT CAC CGG CTG GGC<br>CAA GGT GAT | 28 |
| axmi115sub14 a | ATC ACC TTG GCC CAG CCG GTG ACG<br>GAG AAG TTC ACC CTG TAG GTG CTG<br>TAG CTG TCG | 29 |
| axmi115sub15 s | GCT TCA GCG GCC TCG ACG CCA ATG<br>TGA GGA TCA GAA ACA GCC GCG GC | 30 |

TABLE 2-continued

| Oligo-nucleotide primer | Sequence | SEQ ID NO: |
|---|---|---|
| axmil15sub15 a | GCC GCG GCT GTT TCT GAT CCT CAC ATT GGC GTC GAG GCC GCT GAA GC | 31 |
| axmil15sub16 s | GTG AAG AAC AGC CGC GAG GTG CTC TTC GAG AAG AGA TAC ATG AAT GGA AGC AGC TAT GA | 32 |
| axmil15sub16 a | TCA TAG CTG CTT CCA TTC ATG TAT CTC TTC TCG AAG AGC ACC TCG CGG CTG TTC TTC AC | 33 |
| axmil15sub17 s | TTC GAG AAG GTG AAG AAC AGC GGC GCC AAG GAT GTT TCA GAG AGC TTC ACC ACC | 34 |
| axmil15sub17 a | GGT GGT GAA GCT CTC TGA AAC ATC CTT GGC GCC GCT GTT CTT CAC CTT CTC GAA | 35 |
| axmil15sub19 s | GCT TCT TCA TCG AGC TCA GCC AAG GCA ACA ACC TCT ATA GCA GCA CCT TCC AC | 36 |
| axmil15sub19 a | GTG GAA GGT GCT GCT ATA GAG GTT GTT GCC TTG GCT GAG CTC GAT GAA GAA GC | 37 |
| axmil15sub2 s | GAA GCA AGG CGC TCT ATG TTC ACA AGG ATG GAG GCT TCA GCC AGT TCA TCG | 38 |
| axmil15sub2 a | CGA TGA ACT GGC TGA AGC CTC CAT CCT TGT GAA CAT AGA GCG CCT TGC TTC | 39 |
| axmil15sub20 s | CCG CCG AGA GGA CAG GAG GGC CGC TGG TGA AGT TCA GAG ACA TCA GCA TC | 40 |
| axmil15sub20 a | GAT GCT GAT GTC TCT GAA CTT CAC CAG CGG CCC TCC TGT CCT CTC GGC GG | 41 |
| axmil15sub21 s | AGC ACC TTC CAC AGC TTC AAT GAT GTG AGC ATC AAG TAA GGC GCG CCG | 42 |
| axmil15sub21 a | CGG CGC GCC TTA CTT GAT GCT CAC ATC ATT GAA GCT GTG GAA GGT GCT | 43 |
| axmil15sub3 s | CGA CAA GCT AAA GCC CAA GAC AGA ATA TGT CAT CCA GTA CAC CGT CAA G | 44 |
| axmil15sub3 a | CTT GAC GGT GTA CTG GAT GAC ATA TTC TGT CTT GGG CTT TAG CTT GTC G | 45 |
| axmil15sub5 s | CCT ACG AGG ACA CCA ATA ACA ACA ACC TGG AGG ACT ACC AAA CAA TTG CTG TGA AG | 46 |
| axmil15sub5 a | CTT CAC AGC AAT TGT TTG GTA GTC CTC CAG GTT GTT GTT ATT GGT GTC CTC GTA GG | 47 |
| axmil15sub6 s | GAG GAG TTC CAA ACA ATT ACC AAG AGG TTC ACC ACC GGC ACA GAT TTG AGC CAG ACC | 48 |
| axmil15sub6 a | GGT CTG GCT CAA ATC TGT GCC GGT GGT GAA CCT CTT GGT AAT TGT TTG GAA CTC CTC | 49 |
| axmil15sub7 s | CAC CTC AGA AAC AGA TTT GAA GGG CGT CTA CCT CAT CTT GAA GAG CCA AAA TGG ATA T | 50 |
| axmil15sub7 a | ATA TCC ATT TTG GCT CTT CAA GAT GAG GTA GAC GCC CTT CAA ATC TGT TTC TGA GGT G | 51 |
| axmil15sub9 s | TCC TGG AGG CCA AGC CAT CAG AGA AGC TGC TCA GCC CGG AGC TCA | 52 |
| axmil15sub9 a | TGA GCT CCG GGC TGA GCA GCT TCT CTG ATG GCT TGG CCT CCA GGA | 53 |
| axmil15sub13 s | ATC ATT CAA GAG GAG GCA ACC TCA AGC AGA ACC TCC AGC TTG ACA GCT TCA GCA CCT ACG ACC TCA G | 54 |
| axmil15sub13 a | CTG AGG TCG TAG GTG CTG AAG CTG TCA AGC TGG AGG TTC TGC TTG AGG TTG CCT CCT CTT GAA TGA T | 55 |
| axmil15sub18 s | GCT ATG AGG ACA TCT CAG AGA TCT TCA CCA CAA AGC TGG CAA GG ACA ACT TC TAC A TCG AGC TCA CCG C | 56 |
| axmil15sub18 a | GCG GTG AGC TCG AT GTA G AAG TTG TCC TTG CCC AGC TTG GTG GTG AAG ATC TCT GAG ATG TCC TCA TAG C | 57 |
| axmil15sub4 s | CAA GGG CAA GCC GTC AAT CCA CCT CAA GAA TGA GAA CAC CGG CTA CAT CCA CTAC GA GGA CAC CAA TGG | 58 |
| axmil15sub4 a | CCA TTG GTG TCC TCG TAG TGG ATG TAG CCG GTG TTC TCA TTC TTG AGG TGG ATT GAC GGC TTG CCC TTG | 59 |
| axmil15sub8 s | CAA GAG CCA AAA TGG AGA TGA AGC ATG GGA AGA CAA CTT CAC CAT CCT GGA GAT CTC GCT CTT CGA GAC ACC AGA A | 60 |
| axmil15sub8 a | TTC TGG TGT CTC GAA GAG CGA GAT CTC CAG GAT GGT GAA GTT GTC TCC CCA TGC TTC ATC TCC ATT TTG GCT CTT G | 61 |

Example 12

Additional Assays for Pesticidal Activity

The ability of an insecticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be in a liquid, solid, or slurry form. The material to be tested may be placed upon the surface and then allowed to dry or incorporate into the diet. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests" and "Journal of Economic Entomology" or by discussion with members of the Entomological Society of America (ESA).

Example 13

Vectoring of the Insecticidal Genes of the Invention for Plant Expression

Each of the coding regions of the genes of the invention is connected independently with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

Example 14

Transformation of the Genes of the Invention into Plant Cells by *Agrobacterium*-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 15

Transformation of Maize Cells with the Insecticidal Genes of the Invention

Maize ears are collected 8-12 days after pollination. Embryos are isolated from the ears, and those embryos 0.8- 1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/l nL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240, 842).

DNA constructs designed to express the genes of the invention in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | per Liter | Source |
| --- | --- | --- |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/l of a 5 mg/ml stock solution of Silver Nitrate (Phytotechnology Labs). This recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING

<160> NUMBER OF SEQ ID NOS: 61

<210> SEQ ID NO 1
<211> LENGTH: 2370
<212> TYPE: DNA
<213> ORGANISM: Bacillus thuringiensis

<400> SEQUENCE: 1

```
atgaatatga ataatactaa attaaacgca agggccctac cgagttttat tgattatttt      60
aatggcattt atggatttgc cactggtatc aaagacatta tgaatatgat tttaaaacg     120
gatacaggtg gtaatctaac cttagacgaa atcctaaaga atcagcagtt actaaatgag    180
atttctggta aattggatgg ggtaaatggg agcttaaatg atcttatcgc acagggaaac    240
ttaaatacag aattatctaa ggaaatctta aaaattgcaa atgaacagaa tcaagtctta    300
aatgatgtta taacaaaact cgatgcgata aatacgatgc ttcatatata tctacctaaa    360
attacatcta tgttaagtga tgtaatgaag caaaattatg cgctaagtct gcaaatagaa    420
tacttaagta agcaattgca agaaatttct gataaattag atattattaa cgtaaatgtt    480
cttattaact ctacacttac tgaaattaca cctgcatatc aacggattaa atatgtgaat    540
gaaaaatttg aagaattaac ttttgctaca gaaaccactt taaaagtaaa aaaggatagc    600
tcgcctgctg atattcttga tgagttaact gaattaactg aactagcgaa aagtgttaca    660
aaaaatgacg ttgatggttt tgaattttac cttaatacat ccacgatgt aatggtagga    720
aataatttat tcgggcgttc agcttttaaaa actgcttcag aattaattgc taaagaaaat    780
gtgaaaacaa gtggcagtga agtaggaaat gtttataatt tcttaattgt attaacagct    840
ctacaagcaa aagcttttct tactttaaca acatgccgaa aattattagg cttagcagat    900
attgattata cttctattat gaatgaacat ttaaataagg aaaagagga atttagagta    960
aacatccttc ctacacttc taatactttt tctaatccta attatgcaaa agttaaagga   1020
agtgatgaag atgcaaagat gattgtggaa gctaaaccag acatgcatt ggttgggttt   1080
gaaatgagca atgattcaat cacagtatta aaagtatatg aggctaagct aaaacaaaat   1140
tatcaagttg ataaggattc cttatcggag gttatttatg gtgatatgga taaattattg   1200
tgtccagatc aatctgaaca aatttattat acaaataata tagtatttcc aaatgaatat   1260
gtaattacta aaattgattt tactaagaaa atgaagactt taagatatga ggtaacagct   1320
aattcttatg attcttctac aggagaaatt gacttaaata agaagaaagt agaatcaagt   1380
gaagcggagt ataggacgtt aagtgctaaa gatgatggag tgtatatgcc gttaggtgtc   1440
atcagtgaaa catttttgac tccgattaat gggtttggcc tccaagctga tgaaaattca   1500
agattaatta ctttaacatg taaatcatat ttaagagaac tactgttagc aacagactta   1560
agcaataaag aaactaaatt gatcgtcccg ccaagtggtt ttattagtaa tattgtagaa   1620
aatgggaact tagagggaga aaacttagag ccgtggatag caaataataa gaatgcgtat   1680
gtagatcata caggcggagt gaatggtact agagctttat atgttcataa ggacggagga   1740
ttttcacaat ttattggaga taagttaaaa ccgaaaactg agtatgtaat ccaatatact   1800
gttaaaggaa aaccttctat tcatttaaaa aatgaaaata ctggatatat tcattatgaa   1860
gatacaaata acaatttaga agattatcaa actattacta acgttttac tacaggaact   1920
gatttaaagg gagtgtatt aattttaaaa agtcaaaatg gagatgaagc ctggggagat   1980
aactttacaa tttttggaaat tagtcccttct gaaaagttat taagtccaga attaatcaat   2040
```

-continued gtaaataatt ggattcgcac gggatcaact catattagcg gtaatacact cactctctat 2100
cagggaggag gaggaaatct aaaacaaaac cttcaattag acagtttttc aacttataga 2160
gtgaattttt ctgtgaccgg agatgctaat gtaaggatta gaaattctag ggaagtgtta 2220
tttgaaaaac gatatatgag cggtgctaaa gatgtttctg aaattttcac tacaaaattg 2280
gggaaagata acttttatat agagctttct caagggaata atttatatgg tggtcctctt 2340
gtaaagttta acgatgtctc aattaagtaa 2370

<210> SEQ ID NO 2
<211> LENGTH: 2385
<212> TYPE: DNA
<213> ORGANISM: Bacillus thuringiensis

<400> SEQUENCE: 2
atgaacatga ataatactaa attaagcaca agagccttac caagttttat tgattatttt 60
aatggcattt atggatttgc cactggtatc aaagacatta tgaacatgat ttttaaaacg 120
gatacaggtg gtgatctaac cctagacgaa attttaaaga atcagcagtt actaaatgaa 180
atttctggta aattggatgg ggtaaatgga agcttaaatg atcttatcgc acagggaaac 240
ttaaatacag aattatctaa ggaaatatta aaaattgcaa atgaacaaaa tcaagtttta 300
aatgatgtta ataacaaact tgatgcgata aatacgatgc tgcatatata tctacctaaa 360
attacctcta tgttaagtga tgtaatgaaa caaaattatg cgctaagtct gcaaatagaa 420
tacctaagta aacagttgca agaaatttct gataaattgg atattattaa cgtaaatgta 480
cttattaact ctacacttac tgaaattaca cctgcgtatc aacggattaa atatgtgaac 540
gaaaaatttg aggaattaac ttttgctaca gaaactaatt taaaagtaaa aaaggatggc 600
tctcctgcag atattcttga tgagttaact gagttaactg aactagcgaa aagtgtaaca 660
aaaaatgatg tggatggttt tgaattttat cttaatacat tccacgatgt aatggtaggg 720
aataatttat tcgggcgttc agctttaaaa actgcatcgg aattaattac taaagaaaat 780
gtgaaaacaa gtggcagtga ggtcggaaat gtttataact tcttaattgt attaacagct 840
ctgcaagcaa aagcttttct tactttaaca acatgccgaa aattattagg cttagcagat 900
attgattata cttctattat gaatgaacat ttaaataagg aaaaagagga atttagagta 960
aacatccttc ctacactttc taatactttt tctaatccta attatataaa aactaaagga 1020
agcgatgagg atgcggaagt gattattcaa gctgaaccag gacatgcttt ggtgggattt 1080
gaaatgatta atgatccaag tccagcgtta aaagtgtatc aggctaaact aacaacaaat 1140
tatcaagttg ataagcagtc attatctgaa actgtgtatg gtgatatgga taaaatatta 1200
tgtccagata aatctcaaca aatgtattat ctgcataata taacattccc aaatgaatat 1260
gtgattacag aaattatttt tacaaagaaa aagaacagtt taaggtatga ggtgatagca 1320
aattattatg agttctcttc aggagatatc gacttaaata agaagttagt aaaatcaagt 1380
gaagcagagt atagtacgtt aagtgttagt aacgatgcta tttatatgcc gctaggtgtt 1440
atcagtgaaa catttttgac cccaattaaa ggattcggac taacagttga tgaaagttca 1500
agactggtaa ctttaacgtg taaatcatat ttaagggaaa ttctgttagc aacagattta 1560
agcaataaag caacaaaatt aattgtccca cctaatggtt ttattagtaa tttggtggaa 1620
aatggggata ttgaggctga caacatagaa ccatggaagg gaaataataa aaatgcgtat 1680
gttgatcata caggtggggt gaatggaact aaagctctgt acactcaaga tgatggggaa 1740
ttttcacaat ttattggaga taagttgaaa tcgaaaactg agtatataat tcaatatact 1800

-continued

```
gtaaaaggaa atacttctat ttatttgaaa gataaaaaaa atgaaaatgt tatttatgaa   1860
gataaaaata ataatttaga ggcttttcaa actattacta aaaggtttac tacagaattg   1920
gattcttcag atgtttactt agtgtttaaa tgcaaaaatg gctataaagc ttggggagac   1980
aactttctaa ttacagaaat taggcctaag gaagtggtaa gcccagaatt gataaaagta   2040
gaaaattgga ttggaatggg tggtagtaat catgtaaacc ctgattcact tttgcttttt   2100
acaggtggga ggtcaatttt aaaacaaaat ctccaattag atagttattc aacctataga   2160
gtaagatttt ctttaatggt aattggtaag gctaaggtta ttataaggaa ttcaagtgaa   2220
gtactgtttg aaaaaagtta tgtgaatgat tctgaaggtg ttttagaagg tgtttctgaa   2280
acttttacta caaaatcgat tcaagataac ttctatgtag aactttctaa tgagggcact   2340
tttggaagta aagatgttgc atacttttat aatttttcta ttaga                   2385
```

<210> SEQ ID NO 3
<211> LENGTH: 2409
<212> TYPE: DNA
<213> ORGANISM: Bacillus thuringiensis

<400> SEQUENCE: 3

```
atgaacatga ataatactaa attaaacgca agggccttac caagttttat tgattatttt     60
aatggcattt atggatttgc cactggtatc aaagacatta tgaacatgat tttaaaaacg    120
gatacaggtg gtgatctaac cctagacgaa attttaaaga atcagcagtt actaaatgaa    180
atttctggta aattggatgg ggtaaatggg agcttaaatg atcttatcgc acagggaaac    240
ttaaatacag aattatctaa ggaaatctta aaaattgcaa atgaacaaaa tcaagtttta    300
aatgatgtta ataacaaact agatgcgata aatacgatgc ttaacatata tctacctaaa    360
attacatcta tgttaagcga tgtaatgaaa caaaattatg cgctaagtct gcagatagaa    420
tacctaagta gacagttaca ggaaatttca gataagttag atgttattaa tttaaatgtt    480
ttaattaatt ctactcttac tgaaatcaca ccttcatatc aacgtattaa atatgtaaat    540
gagaaatttg ataaattaac atttgccaca gaaagcactc taagagcaaa acaaggaatt    600
tttaacgagg atagttttga taataatact cttgaaaatt taactgatct agctgaacta    660
gctaaaagta taaccaaaaa tgatgtggat agtttcgaat tttatcttca cacatttcat    720
gatgtattaa ttggaaataa tttatttgga cgatcggctt taaaaacagc ttcagaatta    780
attactaaag acgagataaa gacaagtgga agtgagattg gaaaagttta tagtttctta    840
attgtgctaa cttctttaca agctaaagcc tttctcactt taacaacatg tagaaaatta    900
ttgggcttat cagatattga ttatacttct attatgaatg aacatctaaa taatgaaaaa    960
aatgaatttc gtgataacat acttcctgca ctgtcgaata agttttctaa ccctagctac   1020
gcaaaaacta taggtagtga caattatgca aaagttattt tagaatctga accaggttat   1080
gctttagtcg gattcgaaat tattaatgac ccaatcccgg tattaaaagc gtataaagca   1140
aaactaaaac aaaattatca agttgataat cagtcgttat cagagattgt ttatttagat   1200
atcgataaac tattttgtcc ggaaaattca gaacaaaaat attatactaa aaatctgaca   1260
tttcctgatg gctatgttat tactaaaatt acctttgaaa aaaaactgaa caacctaatt   1320
tatgaagcaa cagcaaattt ttatgaccca tctacaggag atattgactt aaataagaag   1380
caagtggaat ctacttttcc tcaaacggat tatattacta tggatatagg tgatgatgat   1440
ggtatttata tgccgttagg cgttatcagt gaaacgtttt tgactcctat taatagtttt   1500
ggattagaag ttgacgcgaa atcgaaaaca ttaaccttaa aatgtaaatc ttacctgcga   1560
```

-continued

```
gaatatttat tagagtccga tctaaaaaat aaagaaacag gcttgattgc cccgccaaat    1620 gttttatta gtaatgttgt gaaaaattgg gatatagagg aagatagtct agaaccatgg     1680
gtagcaaata acaaaaatgc ctatgttgat aatacaggcg gtatagaaag atctaaagcc    1740
ctctttactc aaggtgacgg ggaattctca caatttattg gtgataaatt aaaacctaat    1800
acagattata ttattcaata tactgtaaaa ggaaaaccag ccatttattt aaaaaataaa    1860
agtactggat atattacgta cgaggataca aacggtaatt ctgaagaatt caaactata    1920 gctgtaaaat tcacttcaga aactgatctt tcacaaactc atttagtttt taaaagtcaa    1980
aatggttatg aggcttgggg agacaatttt attattttag aagctaagct atttgaaact    2040
cctgaaagtc cagaattgat aaaatttaat gattgggaaa gatttggtac tacttacatt    2100
acaggaaatg agcttagaat cgatcatagt cgtggaggtt attttagaca atctcttaat    2160
atagacagtt attcaactta tgatttgagc ttttcttta gtggattatg ggctaaggtt     2220
attgtgaaaa attcccgagg ggtagtattg tttgaaaaag tgaaaaacaa cggttcatca    2280
tatgaagata ttagtgaaag ttttactacc gcatcaaata aggatggatt ttttatagaa    2340
ctaacagccg aaagaacgag ctcaactttc catagctttc gtgatatttc tattaaggaa    2400
aagattgaa                                                            2409
```

<210> SEQ ID NO 4
<211> LENGTH: 789
<212> TYPE: PRT
<213> ORGANISM: Bacillus thuringiensis

<400> SEQUENCE: 4

```
Met Asn Met Asn Thr Lys Leu Asn Ala Arg Ala Leu Pro Ser Phe
 1               5                  10                  15

Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asn Leu Thr Leu
         35                  40                  45

Asp Glu Ile Leu Lys Asn Gln Gln Leu Leu Asn Glu Ile Ser Gly Lys
     50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220
```

```
Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
            245                 250                 255

Ala Lys Glu Asn Val Lys Thr Ser Gly Ser Glu Val Gly Asn Val Tyr
        260                 265                 270

Asn Phe Leu Ile Val Leu Thr Ala Leu Gln Ala Lys Ala Phe Leu Thr
    275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
            325                 330                 335

Lys Val Lys Gly Ser Asp Glu Asp Ala Lys Met Ile Val Glu Ala Lys
        340                 345                 350

Pro Gly His Ala Leu Val Gly Phe Glu Met Ser Asn Asp Ser Ile Thr
    355                 360                 365

Val Leu Lys Val Tyr Glu Ala Lys Leu Lys Gln Asn Tyr Gln Val Asp
370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Thr Asn Asn Ile Val Phe
            405                 410                 415

Pro Asn Glu Tyr Val Ile Thr Lys Ile Asp Phe Thr Lys Lys Met Lys
        420                 425                 430

Thr Leu Arg Tyr Glu Val Thr Ala Asn Ser Tyr Asp Ser Ser Thr Gly
    435                 440                 445

Glu Ile Asp Leu Asn Lys Lys Val Glu Ser Ser Glu Ala Glu Tyr
450                 455                 460

Arg Thr Leu Ser Ala Lys Asp Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
        500                 505                 510

Glu Leu Leu Leu Ala Thr Asp Leu Ser Asn Lys Glu Thr Lys Leu Ile
    515                 520                 525

Val Pro Pro Ser Gly Phe Ile Ser Asn Ile Val Glu Asn Gly Asn Leu
        530                 535                 540

Glu Gly Glu Asn Leu Glu Pro Trp Ile Ala Asn Asn Lys Asn Ala Tyr
545                 550                 555                 560

Val Asp His Thr Gly Gly Val Asn Gly Thr Arg Ala Leu Tyr Val His
            565                 570                 575

Lys Asp Gly Gly Phe Ser Gln Phe Ile Gly Asp Lys Leu Lys Pro Lys
        580                 585                 590

Thr Glu Tyr Val Ile Gln Tyr Thr Val Lys Gly Lys Pro Ser Ile His
    595                 600                 605

Leu Lys Asn Glu Asn Thr Gly Tyr Ile His Tyr Glu Asp Thr Asn Asn
610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
            645                 650                 655
```

```
Ala Trp Gly Asp Asn Phe Thr Ile Leu Glu Ile Ser Pro Ser Glu Lys
            660                 665                 670

Leu Leu Ser Pro Glu Leu Ile Asn Val Asn Asn Trp Ile Arg Thr Gly
            675                 680                 685

Ser Thr His Ile Ser Gly Asn Thr Leu Thr Leu Tyr Gln Gly Gly Gly
            690                 695                 700

Gly Asn Leu Lys Gln Asn Leu Gln Leu Asp Ser Phe Ser Thr Tyr Arg
705                 710                 715                 720

Val Asn Phe Ser Val Thr Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Ile Phe Thr Thr Lys Leu Gly Lys Asp Asn Phe Tyr Ile Glu
            755                 760                 765

Leu Ser Gln Gly Asn Asn Leu Tyr Gly Gly Pro Leu Val Lys Phe Asn
            770                 775                 780

Asp Val Ser Ile Lys
785

<210> SEQ ID NO 5
<211> LENGTH: 795
<212> TYPE: PRT
<213> ORGANISM: Bacillus thuringiensis

<400> SEQUENCE: 5

Met Asn Met Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Asn Leu Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240
```

```
Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Pro Asn Tyr Ile
                325                 330                 335

Lys Thr Lys Gly Ser Asp Glu Asp Ala Glu Val Ile Ile Gln Ala Glu
            340                 345                 350

Pro Gly His Ala Leu Val Gly Phe Glu Met Ile Asn Asp Pro Ser Pro
        355                 360                 365

Ala Leu Lys Val Tyr Gln Ala Lys Leu Thr Thr Asn Tyr Gln Val Asp
    370                 375                 380

Lys Gln Ser Leu Ser Glu Thr Val Tyr Gly Asp Met Asp Lys Ile Leu
385                 390                 395                 400

Cys Pro Asp Lys Ser Gln Gln Met Tyr Tyr Leu His Asn Ile Thr Phe
                405                 410                 415

Pro Asn Glu Tyr Val Ile Thr Glu Ile Ile Phe Thr Lys Lys Lys Asn
            420                 425                 430

Ser Leu Arg Tyr Glu Val Ile Ala Asn Tyr Tyr Glu Phe Ser Ser Gly
        435                 440                 445

Asp Ile Asp Leu Asn Lys Lys Leu Val Lys Ser Glu Ala Glu Tyr
    450                 455                 460

Ser Thr Leu Ser Val Ser Asn Asp Ala Ile Tyr Met Pro Leu Gly Val
465                 470                 475                 480

Ile Ser Glu Thr Phe Leu Thr Pro Ile Lys Gly Phe Gly Leu Thr Val
                485                 490                 495

Asp Glu Ser Ser Arg Leu Val Thr Leu Thr Cys Lys Ser Tyr Leu Arg
            500                 505                 510

Glu Ile Leu Leu Ala Thr Asp Leu Ser Asn Lys Ala Thr Lys Leu Ile
        515                 520                 525

Val Pro Pro Asn Gly Phe Ile Ser Asn Leu Val Glu Asn Gly Asp Ile
    530                 535                 540

Glu Ala Asp Asn Ile Glu Pro Trp Lys Gly Asn Asn Lys Asn Ala Tyr
545                 550                 555                 560

Val Asp His Thr Gly Gly Val Asn Gly Thr Lys Ala Leu Tyr Thr Gln
                565                 570                 575

Asp Asp Gly Glu Phe Ser Gln Phe Ile Gly Asp Lys Leu Lys Ser Lys
            580                 585                 590

Thr Glu Tyr Ile Ile Gln Tyr Thr Val Lys Gly Asn Thr Ser Ile Tyr
        595                 600                 605

Leu Lys Asp Lys Lys Asn Glu Asn Val Ile Tyr Glu Asp Lys Asn Asn
    610                 615                 620

Asn Leu Glu Ala Phe Gln Thr Ile Thr Lys Arg Phe Thr Thr Glu Leu
625                 630                 635                 640

Asp Ser Ser Asp Val Tyr Leu Val Phe Lys Cys Lys Asn Gly Tyr Lys
                645                 650                 655

Ala Trp Gly Asp Asn Phe Leu Ile Thr Glu Ile Arg Pro Lys Glu Val
```

```
                        660                 665                 670
Val Ser Pro Glu Leu Ile Lys Val Glu Asn Trp Ile Gly Met Gly Gly
            675                 680                 685

Ser Asn His Val Asn Pro Asp Ser Leu Leu Phe Thr Gly Gly Arg
        690                 695                 700

Ser Ile Leu Lys Gln Asn Leu Gln Leu Asp Ser Tyr Ser Thr Tyr Arg
705                 710                 715                 720

Val Arg Phe Ser Leu Met Val Ile Gly Lys Ala Lys Val Ile Ile Arg
                725                 730                 735

Asn Ser Ser Glu Val Leu Phe Glu Lys Ser Tyr Val Asn Asp Ser Glu
            740                 745                 750

Gly Val Leu Glu Gly Val Ser Glu Thr Phe Thr Lys Ser Ile Gln
        755                 760                 765

Asp Asn Phe Tyr Val Glu Leu Ser Asn Glu Gly Thr Phe Gly Ser Lys
        770                 775                 780

Asp Val Ala Tyr Phe Tyr Asn Phe Ser Ile Arg
785                 790                 795

<210> SEQ ID NO 6
<211> LENGTH: 803
<212> TYPE: PRT
<213> ORGANISM: Bacillus thuringiensis

<400> SEQUENCE: 6

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
        210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
```

```
                245                 250                 255
Ala Ser Glu Leu Ile Thr Lys Asp Glu Ile Lys Thr Ser Gly Ser Glu
                260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
            530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Glu Phe Ser Gln Phe
            580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
            610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
            660                 665                 670
```

```
Leu Glu Ala Lys Leu Phe Glu Thr Pro Glu Ser Pro Glu Leu Ile Lys
            675                 680                 685
Phe Asn Asp Trp Glu Arg Phe Gly Thr Thr Tyr Ile Thr Gly Asn Glu
        690                 695                 700
Leu Arg Ile Asp His Ser Arg Gly Gly Tyr Phe Arg Gln Ser Leu Asn
705                 710                 715                 720
Ile Asp Ser Tyr Ser Thr Tyr Asp Leu Ser Phe Ser Phe Ser Gly Leu
                725                 730                 735
Trp Ala Lys Val Ile Val Lys Asn Ser Arg Gly Val Val Leu Phe Glu
            740                 745                 750
Lys Val Lys Asn Asn Gly Ser Ser Tyr Glu Asp Ile Ser Glu Ser Phe
        755                 760                 765
Thr Thr Ala Ser Asn Lys Asp Gly Phe Phe Ile Glu Leu Thr Ala Glu
    770                 775                 780
Arg Thr Ser Ser Thr Phe His Ser Phe Arg Asp Ile Ser Ile Lys Glu
785                 790                 795                 800
Lys Ile Glu

<210> SEQ ID NO 7
<211> LENGTH: 2388
<212> TYPE: DNA
<213> ORGANISM: Artificial Sequence
<220> FEATURE:
<223> OTHER INFORMATION: synthetic nucleotide sequence encoding AXMI-005
      w/ c-terminal extension

<400> SEQUENCE: 7
atgaacatga acaacaccaa gctcaatgca agggcgctgc cgagcttcat cgactacttc      60
aatggcatct atggcttcgc caccggcatc aaggacatca tgaacatgat cttcaagacc     120
gacaccggcg gcaacctcac cttggatgag atcctcaaga accagcagct gctgaatgag     180
atctcaggca gctggacggg cgtcaatgga gccctcaacg acctcattgc tcaaggcaac     240
ctcaacaccg agctgagcaa ggagatcctc aagattgcaa atgagcagaa ccaggtgctg     300
aatgatgtca acaacaagct ggacgccatc aacaccatgc tgcacatcta cctgccaaag     360
atcacctcaa tgctctctga tgtgatgaag cagaactacg cgctgagcct ccagattgag     420
tacctctcaa gcagctgca agagatctcc gacaagctgg acatcatcaa tgtcaatgtg     480
ctcatcaaca gcaccttgac agagatcacg ccggcctacc agaggatcaa gtatgtcaat     540
gagaagtttg aggagctcac cttcgccacc gagacaacat tgaaggtgaa gaaggacagc     600
tcgccggcgg acatcctgga tgagctcacc gagctaacag agctggccaa gagcgtcacc     660
aagaatgatg ttgatggctt cgagttctac ctcaacaccc tccatgatgt gatggtgggc     720
aacaacctct tcggccgctc ggcgctcaag acggcgtcgg agctgatcgc caaggagaat     780
gtcaagacaa gtggatcaga ggtgggcaat gtctacaact tcctcatcgt gctgacggcg     840
ctgcaagcca aggccttcct caccttgaca acctgccgca gttgctgggc cctcgccgac     900
atcgactaca cctccatcat gaatgagcac ctcaacaagg agaaggagga gttccgcgtc     960
aacatcctgc aacattgag caacaccttc agcaacccca actacgccaa ggtgaagggc    1020
tcagatgaag atgccaagat gattgtggag gccaagcctg ccatgctct ggtgggcttc     1080
gagatgagca cgacagcat caccgtgctg aaggtctacg aggccaagct gaagcagaac    1140
taccaggtgg acaaggacag cttgtctgag gtgatctacg cgacatggga caagctgcta    1200
tgtccagatc aaagcgagca gatctactac accaacaaca tcgtctttcc aaatgaatat    1260
gtcatcacca agatcgactt caccaagaag atgaaaacat tgagatatga ggtgacggcc    1320
```

```
aacagctacg acagcagcac cggcgagatc gacctcaaca agaagaaggt ggagagctca    1380
gaagctgagt acaggacgct ctccgccaag gatgatggcg tctacatgcc gctcggcgtc    1440
atctcagaaa ccttcttgac gcccatcaat ggcttcggcc tccaagctga tgagaacagc    1500
aggctcatca ccttgacctg caagagctac ctcagggagc tgctgctggc caccgacctc    1560
agcaacaagg agacaaagct catcgtgccg ccatcaggct tcatcagcaa catcgtggag    1620
aatggcaacc tggaaggaga gaacctggag ccatggatag ccaacaacaa gaatgcttat    1680
gttgatcaca ccggcggcgt caatggaaca agggcgctct atgttcacaa ggatggaggc    1740
ttcagccagt tcatcggcga caagctgaag cccaagacag aatatgtcat ccagtacacc    1800
gtcaagggca agccatcaat ccacctcaag aatgagaaca ccggctacat ccactacgag    1860
gacaccaaca acaacctgga ggactaccag accatcacca gaggttcac caccggcacc     1920 gacctcaagg gcgtctacct catcttgaag agccaaaatg gagatgaagc atggggagac    1980
aacttcacca tcctggagat ctcgccatca gagaagctgc tctcgccgga gctcatcaat    2040
gtcaacaact ggatcagaac tggaagcacc cacatcagcg gcaacacctt gacgctctac    2100
caaggaggag gaggcaacct caagcagaac ctccagcttg acagcttctc cacctacagg    2160
gtgaacttct ccgtcaccgg cgacgccaat gtgaggatca gaaattcaag ggaggtgctc    2220
ttcgagaaga gatacatgag cggcgccaag gatgtttctg agatcttcac caccaagctg    2280
ggcaaggaca acttctacat cgagctgagc caaggcaaca acctctatgg agggccgctg    2340
gtgaagttca atgatgtgag catcaagcat caccaccatc atcactaa                 2388
```

<210> SEQ ID NO 8
<211> LENGTH: 2430
<212> TYPE: DNA
<213> ORGANISM: Artificial Sequence
<220> FEATURE:
<223> OTHER INFORMATION: synthetic nucleotide sequence encoding AXMI-113
      w/ c-terminal extension

<400> SEQUENCE: 8

```
atgaacatga caacaccaa gctcaatgca agggcgctgc cgagcttcat cgactacttc      60
aatggcatct atggcttcgc caccggcatc aaggacatca tgaacatgat cttcaagacc    120
gacaccggcg cgacctcac cttggatgag atcctcaaga accagcagct gctgaatgag     180
atctcaggca agctggacgg cgtcaatgga agcctcaacg acctcattgc tcaaggcaac    240
ctcaacaccg agctgagcaa ggagatcctc aagattgcaa atgagcagaa ccaggtgctg    300
aatgatgtca caacaagct ggacgccatc aacaccatgc tcaacatcta cctgccaaag    360
atcacctcaa tgctctctga tgtgatgaag cagaactacg cgctgagcct ccagattgag    420
tacctctcaa ggcagctgca agagatctcc gacaagctgg atgtcatcaa cctcaatgtg    480
ctcatcaaca gcaccttgac agagatcacg ccaagctacc agaggatcaa gtatgtcaat    540
gagaagttcg acaagctcac cttcgccacc gagagcaccc tccgcgccaa gcaaggcatc    600
ttcaatgaag attcatttga caacaacacc ttggagaact tgacagacct cgccgagctg    660
gccaagagca tcaccaagaa tgatgtggac agcttcgagt tctacctcca caccttccat    720
gatgtgctca tcggcaacaa cctctttgga agaagcgcgc tcaagacggc atcgagctc    780 atcaccaagg atgagatcaa gacaagcggc agcgagatcg caaggtctac agcttcctc    840 atcgtgctga catcattgca agccaaggcc ttcctcacct tgacaacctg ccgcaagttg    900
ctgggcctct ccgacatcga ctacacctcc atcatgaatg agcacctcaa caatgagaag    960
```

```
aatgagttca gagacaacat cctgccggcg ctgagcaaca agttcagcaa cccaagctac   1020
gccaagacca tcggctcaga caactacgcc aaggtgatcc tggagagcga gcctggctac   1080
gcgctggtgg gcttcgagat catcaatgat ccaattcctg ttctcaaggc ctacaaggcc   1140
aagctgaagc agaactacca ggtggacaac cagagcttga gcgagatcgt ctacctggac   1200
atcgacaagc tcttctgccc ggagaactca gagcagaagt actacaccaa gaacctcacc   1260
ttccctgatg gatatgtcat caccaagatc accttcgaga agaagctgaa caacctcatc   1320
tacgaggcca ccgccaactt ctatgatcca tcaacaggag acatcgacct caacaagaag   1380
caagtggaga gcaccttccc tcaaacagac tacatcacca tggacattgg agatgatgat   1440
ggcatctaca tgccgctcgg cgtcatctca gaaaccttct tgacgcccat caacagcttc   1500
ggcctggagg tggacgccaa gagcaagacc ttgacgctca agtgcaagag ctacctcagg   1560
gagtacctgc tggagagtga tttgaagaac aaggagacag gctgatcgc ccgccaaat   1620 gtgttcatca gcaatgtggt gaagaactgg gacatcgagg aggattcatt ggagccatgg   1680
gtggccaaca acaagaatgc ttatgtggac aacaccggcg gcattgaaag aagcaaggcg   1740
ctcttcaccc aaggagatgg agagttcagc cagttcatcg gcgacaagct aaagcccaac   1800
accgactaca tcatccagta caccgtcaag ggcaagccgg ccatctacct caagaacaag   1860
agcaccggct acatcaccta cgaggacacc aatggaaatt ctgaggagtt ccaaacaatt   1920
gctgtgaagt tcacctcaga aacagatttg agccagaccc acctggtgtt caagagccaa   1980
aatggatatg aagcatgggg agacaacttc atcatcctgg aggccaagct cttcgagaca   2040
ccagaaagcc cggagctcat caagttcaat gattgggaga ggttcggcac cacctacatc   2100
accggcaatg agctgaggat tgatcattca gaggaggct acttccgcca agcctcaac   2160 atcgacagct acagcaccta cgacctcagc ttcagcttca gcggcctctg ggccaaggtg   2220
attgtgaaga acagccgcgg cgtggtgctc ttcgagaagg tgaagaacaa tggaagcagc   2280
tatgaggaca tctcagagag cttcaccacc gccagcaaca aggatggctt cttcatcgag   2340
ctcaccgccg agaggacaag cagcaccttc cacagcttca gagacatcag catcaaggag   2400
aagattgaac atcaccacca tcatcactaa                                    2430
```

<210> SEQ ID NO 9
<211> LENGTH: 795
<212> TYPE: PRT
<213> ORGANISM: Artificial Sequence
<220> FEATURE:
<223> OTHER INFORMATION: AXMI-005 w/ c-terminal extension

<400> SEQUENCE: 9

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asn Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110
```

```
Met Leu His Ile Tyr Leu Pro Lys Ile Thr Ser Met Leu Ser Asp Val
            115                 120                 125
Met Lys Gln Asn Tyr Ala Leu Ser Leu Gln Ile Glu Tyr Leu Ser Lys
        130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Glu Glu Leu Thr Phe Ala Thr Glu Thr
            180                 185                 190
Thr Leu Lys Val Lys Lys Asp Ser Ser Pro Ala Asp Ile Leu Asp Glu
        195                 200                 205
Leu Thr Glu Leu Thr Glu Leu Ala Lys Ser Val Thr Lys Asn Asp Val
    210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Ala Lys Glu Asn Val Lys Thr Ser Ser Glu Val Gly Asn Val Tyr
            260                 265                 270
Asn Phe Leu Ile Val Leu Thr Ala Leu Gln Ala Lys Ala Phe Leu Thr
        275                 280                 285
Leu Thr Thr Cys Arg Lys Leu Leu Gly Leu Ala Asp Ile Asp Tyr Thr
    290                 295                 300
Ser Ile Met Asn Glu His Leu Asn Lys Glu Lys Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Val Gly Phe Glu Met Ser Asn Asp Ser Ile Thr
        355                 360                 365
Val Leu Lys Val Tyr Glu Ala Lys Leu Lys Gln Asn Tyr Gln Val Asp
    370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Met Lys
            420                 425                 430
Thr Leu Arg Tyr Glu Val Thr Ala Asn Ser Tyr Asp Ser Ser Thr Gly
        435                 440                 445
Glu Ile Asp Leu Asn Lys Lys Val Glu Ser Ser Glu Ala Glu Tyr
    450                 455                 460
Arg Thr Leu Ser Ala Lys Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Gly Asn Leu
```

530                 535                 540
Glu Gly Glu Asn Leu Glu Pro Trp Ile Ala Asn Asn Lys Asn Ala Tyr
545                 550                 555                 560

Val Asp His Thr Gly Gly Val Asn Gly Thr Arg Ala Leu Tyr Val His
                    565                 570                 575

Lys Asp Gly Gly Phe Ser Gln Phe Ile Gly Asp Lys Leu Lys Pro Lys
                    580                 585                 590

Thr Glu Tyr Val Ile Gln Tyr Thr Val Lys Gly Lys Pro Ser Ile His
                    595                 600                 605

Leu Lys Asn Glu Asn Thr Gly Tyr Ile His Tyr Glu Asp Thr Asn Asn
                    610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                    645                 650                 655

Ala Trp Gly Asp Asn Phe Thr Ile Leu Glu Ile Ser Pro Ser Glu Lys
                    660                 665                 670

Leu Leu Ser Pro Glu Leu Ile Asn Val Asn Asn Trp Ile Arg Thr Gly
                    675                 680                 685

Ser Thr His Ile Ser Gly Asn Thr Leu Thr Leu Tyr Gln Gly Gly Gly
                    690                 695                 700

Gly Asn Leu Lys Gln Asn Leu Gln Leu Asp Ser Phe Ser Thr Tyr Arg
705                 710                 715                 720

Val Asn Phe Ser Val Thr Gly Asp Ala Asn Val Arg Ile Arg Asn Ser
                    725                 730                 735

Arg Glu Val Leu Phe Glu Lys Arg Tyr Met Ser Gly Ala Lys Asp Val
                    740                 745                 750

Ser Glu Ile Phe Thr Thr Lys Leu Gly Lys Asp Asn Phe Tyr Ile Glu
                    755                 760                 765

Leu Ser Gln Gly Asn Asn Leu Tyr Gly Gly Pro Leu Val Lys Phe Asn
                    770                 775                 780

Asp Val Ser Ile Lys His His His His His
785                 790                 795

<210> SEQ ID NO 10
<211> LENGTH: 809
<212> TYPE: PRT
<213> ORGANISM: Artificial Sequence
<220> FEATURE:
<223> OTHER INFORMATION: AXMI-113 w/ c-terminal extension

<400> SEQUENCE: 10

Met Asn Met Asn Asn Thr Lys Leu Asn Ala Arg Ala Leu Pro Ser Phe
 1               5                  10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
                35                  40                  45

Asp Glu Ile Leu Lys Asn Gln Gln Leu Leu Asn Glu Ile Ser Gly Lys
                50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
                100                 105                 110

```
Met Leu Asn Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
                180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
                260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
    370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
        435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
```

```
                530             535             540
Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Glu Phe Ser Gln Phe
                580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
            610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
                660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu His His His His His His
                805
```

<210> SEQ ID NO 11
<211> LENGTH: 2370
<212> TYPE: DNA
<213> ORGANISM: Bacillus thuringiensis

<400> SEQUENCE: 11

```
gtgagggtaa acatgcagaa aaataataaa ttaagtgtaa gggctttacc aagtttcatt      60
gattatttta atgggattta cggattcgcc actggtatca agatattat gaacatgatt      120 tttaaaacga atacaggagg ggatctaacc ttagacgaaa tattaaaaaa tcaacagtta     180
cttaatgaga tttctggcaa actggatgga gtgaatggca gcttaaatga tcttctcgca     240
caaggaaact tgaatactga attatctaag gaaatattaa aaattgcaaa tgaacagaat     300
agggttttaa atgatgtaaa tacaaagctt gatgcgataa atttaatgct aacacatat      360 ttacctaaaa ttacttctat gttaagtgat gtaatgaagc aaaattatgc attaggtttg     420
cagatagaat acctaagcaa acaattaaag gaaatttcag ataagctaga tgttattaat     480
gtaaatgtac tcattaactt tacacttact gaaattcac ctgcctatca aaggattaaa      540
tatgtaaatg aaaaatttga agcattaacc tctgctacag aaaccaattt aaaaacaaaa     600
```

```
caagatagct ctcatacaga tattcttgat gagttaacag agctaacgga actagcgaaa    660
agtgtaacaa aaaatgacgt ggatggcttt gaattttacc ttaatacatt ccacgatgta    720
atgattggga ataatctatt tggacgttca gctttaaaaa cagcctcgga attaattgcg    780
aaagaaaatt tgaaaacaag tggcagtgag gtaggaaatg tttataattt cttaattgta    840
ttaacagctc tgcaagcaaa agcttttctt actttaacta catgccggaa attattgggc    900
ttagcagata ttgattatac tcctattatg aatgaacacc taaataaaga aaagaggaa     960 tttagagtga acatccttcc tacactttct aatactttt ctaatcctaa ttatgaaaaa    1020
gctagaggga gtgataagga tgcgaaaatc attatggaag ctaaacctgg atatgcttta   1080
gttggatttg aaataagtaa ggattcaatt gcagtattaa agtttatca ggcaaagcta    1140 aaacacaact atcaaattga taaggattcg ttatcagaaa ttgtttatgg tgatatagat   1200
aaattattat gtccggatca atctgaacaa atgtattata caaataaaat agctttcca   1260 aatgaatatg ttatcactaa aattgctttt actaaaaaac tgaacagttt aagatatgag   1320
gtcacagcga attttttatga ctcttctaca ggagatattg atctaaataa gaaaaaaata   1380
gaatcaagtg aggcggagtt tagtatgcta atgctaata atgagggtgt ttatatgccg    1440
ataggtacta aagtgaaaac attttttgact ccaattaatg gatttggcct cgtagtcgat   1500
gaaaattcaa gactagtaac tttgacatgt aaatcatatt taagagagac attgttagca   1560
acagacttaa gtaataaaga aactaaactg attgtcccac ctaatggttt tattagcaat   1620
attgtagaaa atgggaactt agagggagaa aacttagagc cgtggaaagc aaataacaaa   1680
aatgcgtatg tagatcatac cggaggtgta atggaactaa agttttata tgttcatgag    1740 gatggtgagt tctcacaatt tattggggaa aaattgaaat tgaaaacaga atatgtaatt   1800
caatatattg taagggaaa agctgctatt tatttaaaag atgaaaaaa tggggattac    1860 atttatgaag aaacaaataa tgaattagaa gattttcaaa ctgttactaa acgttttatt   1920
acgggaacag attcttcaag agttcattta attttttacca gtcaaaatgg cgaggaagca   1980
tttggaggaa actttattat ttcagaaatt aggccatccg aagagttatt aagtccagaa   2040
ttgattaagt tggatgcttg ggttggatct cagggaactt ggatctcagg aaattctctc   2100
aatattaata gtaatgtaaa tggaaccttt cgacaaaacc tttcgttaga aagttattca   2160
acctatagta tgaactttaa tgtgaatgga tttggcaagg tgacaataag aaattctcgt   2220
gaagtagtat ttgaaaggag ttatctacag ttttcctcta aatatatttc agaaaaattc   2280
acaacaacaa ccaataatac tgggttatat gtagaacttt ctcgtgcttc gtctggggga   2340
gttataaatt tcggagattt ttcaatcaag                                     2370
```

<210> SEQ ID NO 12
<211> LENGTH: 2370
<212> TYPE: DNA
<213> ORGANISM: Bacillus thuringiensis

<400> SEQUENCE: 12

```
atgaacatga acaagaataa tactaaatta agcgcaagag ctttaccaag ttttattgat     60
tattttaatg gcatttatgg atttgccact ggcatcaaag atattatgaa catgattttt    120
aaaacggata caggtggtga tctaacccta gacgaaattt aaagaatca gcagttacta    180 aatgatattt ctggtaaatt ggatggggtg aatggaagct taaatgatct tatcgcacag    240
ggaaacttaa atacagaatt atctaaggaa atattaaaaa ttgcaaatga acaaaatcaa    300
gttttaaatg atgttaataa caaactcgat gcgataaata cgatgcttca tgtatatcta    360
```

```
cctaaaatta cctctatgtt aagtgatgta atgaaaccaa attatgcgct aagtatgcaa    420
atagaatacc taagtagaca attacaagaa atttcagata agctagatat tatcaacgta    480
aatgtactta ttaactctac acttactgaa attcacctg cgtatcaatg gattaaatat     540
gtgaacgaaa aatttgaaga attaactttt gctacagaaa ctactttaaa agtaaaaaat    600
gatagcgctt ctgcagatat tcttgatgag ttaacggagt taactgaact tgcgaaaagt    660
gtaacaaaaa atgatgtgga tggttttgaa ttttaccttta atacattcca cgatgtaatg    720
gtaggaaata atttattcgg gcgttcgact ttaaaaactg cttcggaatt aattgctaaa    780
gaaaatgtga aaacaagtgg cagtgaggta ggaaatgttt ataatttctt agttgtatta    840
acagctctac aagcaaaagc ttttcttact ttaacaacat gccgaaaatt attaggccta    900
gcagatattg attatacatc tattatgaat gaacatttaa ataaggaaaa agaggaattt    960
agagtaaaca tccttcctat actttctaat acttttcta atcctaatta tgcaaaagtt     1020
aaaggaagtg atgaagatgc aaagatgatt gtggaagcta aaccaggaca tgcattggtt    1080
gggtttgaaa ttagtaatga ttcaatgaca gtattaaaag tatatgaagc taagctaaaa    1140
caaaattacc aagttgataa ggattcctta tcggaagtca tttatggtga tatggataaa    1200
ttattgtgcc cagatcaatc tgaaaaaatt tattatacaa ataatatagt atttccaaat    1260
gaatatgtaa ttactaaaat tgattttact aagaaaatga aaactttaag atatgaggta    1320
acagctaatt cttatgattc ttctacagga gaaattgact aaataaaaa gaaagtagaa     1380 tcaagtaaag cggagtatag gacgttaagt gctaataatg atggagtata tatgccgtta    1440
ggtgtcatca gtgaaacatt tttgactcca attaatggat ttggcctcca agctgatgaa    1500
aattcaagat taattacttt aacgtgtaaa tcatatttaa gggaactact actagcgaca    1560
gacttaagca ataagaaac taaattgatt gtcccgccaa atagttttat tagcaatatt    1620
gtagagaatg ggtccataga agagggccac ttagagcctt ggaaagcaaa taataagaac    1680
gcttatgtag atcatacagg cggagtgaat ggtactaaag ctctatatgt tcatgaggat    1740
gggggggttt cacaatttat gggagataaa ttaaaaccga aaactgagta tgtaattcaa    1800
tatactgtta aaggaaaacc ttctattcat ttaaaagatg aaaatactgg atatattctt    1860
tatgaagata caaataatga tttagaagat ttccaaacta taactaaaag gttcacaaca    1920
ggaactgatt taatgagagt gtatttaatt ttaaaaagtc aaagtggtca cgaagcttgg    1980
ggagataact ttacaatttt ggaaattaag cctgcggagg ctttagtaag cccagaattg    2040
attaatccga attcttggat tacaactcaa ggggctagca tttcaggaga taaacttttt    2100
attagcttgg ggacaaatgg gacctttaga caaaatcttt cattaaacag ttattcaact    2160
tatagtataa gctttactgc atcgggacca tttaatgtga cggtaagaaa ttctagggaa    2220
gtattatatg aacgaaacaa ccttatgtct tcaactagtc atatttctgg ggaattcaaa    2280
actgaatcca ataataccgg attatatgta gaactttccc gtcgttctgg tggtgctggt    2340
catatatcat ttgaaaacat ttctattaaa                                    2370
```

<210> SEQ ID NO 13
<211> LENGTH: 790
<212> TYPE: PRT
<213> ORGANISM: Bacillus thuringiensis

<400> SEQUENCE: 13

```
Met Arg Val Asn Met Gln Lys Asn Asn Lys Leu Ser Val Arg Ala Leu
1               5                   10                  15
```

```
Pro Ser Phe Ile Asp Tyr Phe Asn Gly Ile Tyr Gly Phe Ala Thr Gly
            20                  25                  30

Ile Lys Asp Ile Met Asn Met Ile Phe Lys Thr Asn Thr Gly Gly Asp
        35                  40                  45

Leu Thr Leu Asp Glu Ile Leu Lys Asn Gln Gln Leu Leu Asn Glu Ile
 50                  55                  60

Ser Gly Lys Leu Asp Gly Val Asn Gly Ser Leu Asn Asp Leu Leu Ala
 65                  70                  75                  80

Gln Gly Asn Leu Asn Thr Glu Leu Ser Lys Glu Ile Leu Lys Ile Ala
                85                  90                  95

Asn Glu Gln Asn Arg Val Leu Asn Asp Val Asn Thr Lys Leu Asp Ala
                100                 105                 110

Ile Asn Leu Met Leu Asn Thr Tyr Leu Pro Lys Ile Thr Ser Met Leu
            115                 120                 125

Ser Asp Val Met Lys Gln Asn Tyr Ala Leu Gly Leu Gln Ile Glu Tyr
 130                 135                 140

Leu Ser Lys Gln Leu Lys Glu Ile Ser Asp Lys Leu Asp Val Ile Asn
145                 150                 155                 160

Val Asn Val Leu Ile Asn Phe Thr Leu Thr Glu Ile Thr Pro Ala Tyr
                165                 170                 175

Gln Arg Ile Lys Tyr Val Asn Glu Lys Phe Glu Ala Leu Thr Ser Ala
                180                 185                 190

Thr Glu Thr Asn Leu Lys Thr Lys Gln Asp Ser Ser His Thr Asp Ile
            195                 200                 205

Leu Asp Glu Leu Thr Glu Leu Thr Glu Leu Ala Lys Ser Val Thr Lys
 210                 215                 220

Asn Asp Val Asp Gly Phe Glu Phe Tyr Leu Asn Thr Phe His Asp Val
225                 230                 235                 240

Met Ile Gly Asn Asn Leu Phe Gly Arg Ser Ala Leu Lys Thr Ala Ser
                245                 250                 255

Glu Leu Ile Ala Lys Glu Asn Leu Lys Thr Ser Gly Ser Glu Val Gly
            260                 265                 270

Asn Val Tyr Asn Phe Leu Ile Val Leu Thr Ala Leu Gln Ala Lys Ala
            275                 280                 285

Phe Leu Thr Leu Thr Thr Cys Arg Lys Leu Leu Gly Leu Ala Asp Ile
290                 295                 300

Asp Tyr Thr Pro Ile Met Asn Glu His Leu Asn Lys Glu Lys Glu Glu
305                 310                 315                 320

Phe Arg Val Asn Ile Leu Pro Thr Leu Ser Asn Thr Phe Ser Asn Pro
                325                 330                 335

Asn Tyr Glu Lys Ala Arg Gly Ser Asp Lys Asp Ala Lys Ile Ile Met
            340                 345                 350

Glu Ala Lys Pro Gly Tyr Ala Leu Val Gly Phe Glu Ile Ser Lys Asp
            355                 360                 365

Ser Ile Ala Val Leu Lys Val Tyr Gln Ala Lys Leu Lys His Asn Tyr
370                 375                 380

Gln Ile Asp Lys Asp Ser Leu Ser Glu Ile Val Tyr Gly Asp Ile Asp
385                 390                 395                 400

Lys Leu Leu Cys Pro Asp Gln Ser Glu Gln Met Tyr Tyr Thr Asn Lys
                405                 410                 415

Ile Ala Phe Pro Asn Glu Tyr Val Ile Thr Lys Ile Ala Phe Thr Lys
            420                 425                 430

Lys Leu Asn Ser Leu Arg Tyr Glu Val Thr Ala Asn Phe Tyr Asp Ser
            435                 440                 445
```

Ser Thr Gly Asp Ile Asp Leu Asn Lys Lys Ile Glu Ser Ser Glu
    450                 455                 460

Ala Glu Phe Ser Met Leu Asn Ala Asn Glu Gly Val Tyr Met Pro
465                 470                 475                 480

Ile Gly Thr Ile Ser Glu Thr Phe Leu Thr Pro Ile Asn Gly Phe Gly
                485                 490                 495

Leu Val Val Asp Glu Asn Ser Arg Leu Val Thr Leu Thr Cys Lys Ser
                500                 505                 510

Tyr Leu Arg Glu Thr Leu Leu Ala Thr Asp Leu Ser Asn Lys Glu Thr
                515                 520                 525

Lys Leu Ile Val Pro Pro Asn Gly Phe Ile Ser Asn Ile Val Glu Asn
    530                 535                 540

Gly Asn Leu Glu Gly Glu Asn Leu Glu Pro Trp Lys Ala Asn Asn Lys
545                 550                 555                 560

Asn Ala Tyr Val Asp His Thr Gly Gly Val Asn Gly Thr Lys Val Leu
                565                 570                 575

Tyr Val His Glu Asp Gly Gly Phe Ser Gln Phe Ile Gly Glu Lys Leu
                580                 585                 590

Lys Leu Lys Thr Glu Tyr Val Ile Gln Tyr Ile Val Lys Gly Lys Ala
                595                 600                 605

Ala Ile Tyr Leu Lys Asp Glu Lys Asn Gly Asp Tyr Ile Tyr Glu Glu
    610                 615                 620

Thr Asn Asn Glu Leu Glu Asp Phe Gln Thr Val Thr Lys Arg Phe Ile
625                 630                 635                 640

Thr Gly Thr Asp Ser Ser Arg Val His Leu Ile Phe Thr Ser Gln Asn
                645                 650                 655

Gly Glu Glu Ala Phe Gly Gly Asn Phe Ile Ile Ser Glu Ile Arg Pro
                660                 665                 670

Ser Glu Glu Leu Leu Ser Pro Glu Leu Ile Lys Leu Asp Ala Trp Val
                675                 680                 685

Gly Ser Gln Gly Thr Trp Ile Ser Gly Asn Ser Leu Asn Ile Asn Ser
    690                 695                 700

Asn Val Asn Gly Thr Phe Arg Gln Asn Leu Ser Leu Glu Ser Tyr Ser
705                 710                 715                 720

Thr Tyr Ser Met Asn Phe Asn Val Asn Gly Phe Gly Lys Val Thr Ile
                725                 730                 735

Arg Asn Ser Arg Glu Val Val Phe Glu Arg Ser Tyr Leu Gln Phe Ser
                740                 745                 750

Ser Lys Tyr Ile Ser Glu Lys Phe Thr Thr Thr Asn Asn Thr Gly
                755                 760                 765

Leu Tyr Val Glu Leu Ser Arg Ala Ser Ser Gly Val Ile Asn Phe
    770                 775                 780

Gly Asp Phe Ser Ile Lys
785                 790

<210> SEQ ID NO 14
<211> LENGTH: 790
<212> TYPE: PRT
<213> ORGANISM: Bacillus thuringiensis

<400> SEQUENCE: 14

Met Asn Met Asn Lys Asn Asn Thr Lys Leu Ser Ala Arg Ala Leu Pro
1               5                   10                  15

Ser Phe Ile Asp Tyr Phe Asn Gly Ile Tyr Gly Phe Ala Thr Gly Ile
                20                  25                  30

Lys Asp Ile Met Asn Met Ile Phe Lys Thr Asp Thr Gly Gly Asp Leu
        35                  40                  45

Thr Leu Asp Glu Ile Leu Lys Asn Gln Gln Leu Leu Asn Asp Ile Ser
    50                  55                  60

Gly Lys Leu Asp Gly Val Asn Gly Ser Leu Asn Asp Leu Ile Ala Gln
65                  70                  75                  80

Gly Asn Leu Asn Thr Glu Leu Ser Lys Glu Ile Leu Lys Ile Ala Asn
                85                  90                  95

Glu Gln Asn Gln Val Leu Asn Asp Val Asn Asn Lys Leu Asp Ala Ile
            100                 105                 110

Asn Thr Met Leu His Val Tyr Leu Pro Lys Ile Thr Ser Met Leu Ser
        115                 120                 125

Asp Val Met Lys Pro Asn Tyr Ala Leu Ser Met Gln Ile Glu Tyr Leu
    130                 135                 140

Ser Arg Gln Leu Gln Glu Ile Ser Asp Lys Leu Asp Ile Ile Asn Val
145                 150                 155                 160

Asn Val Leu Ile Asn Ser Thr Leu Thr Glu Ile Thr Pro Ala Tyr Gln
                165                 170                 175

Trp Ile Lys Tyr Val Asn Glu Lys Phe Glu Glu Leu Thr Phe Ala Thr
            180                 185                 190

Glu Thr Thr Leu Lys Val Lys Asn Asp Ser Ala Ser Ala Asp Ile Leu
        195                 200                 205

Asp Glu Leu Thr Glu Leu Thr Glu Leu Ala Lys Ser Val Thr Lys Asn
    210                 215                 220

Asp Val Asp Gly Phe Glu Phe Tyr Leu Asn Thr Phe His Asp Val Met
225                 230                 235                 240

Val Gly Asn Asn Leu Phe Gly Arg Ser Thr Leu Lys Thr Ala Ser Glu
                245                 250                 255

Leu Ile Ala Lys Glu Asn Val Lys Thr Ser Gly Ser Glu Val Gly Asn
            260                 265                 270

Val Tyr Asn Phe Leu Val Val Leu Thr Ala Leu Gln Ala Lys Ala Phe
        275                 280                 285

Leu Thr Leu Thr Thr Cys Arg Lys Leu Leu Gly Leu Ala Asp Ile Asp
    290                 295                 300

Tyr Thr Ser Ile Met Asn Glu His Leu Asn Lys Glu Lys Glu Glu Phe
305                 310                 315                 320

Arg Val Asn Ile Leu Pro Ile Leu Ser Asn Thr Phe Ser Asn Pro Asn
                325                 330                 335

Tyr Ala Lys Val Lys Gly Ser Asp Glu Asp Ala Lys Met Ile Val Glu
            340                 345                 350

Ala Lys Pro Gly His Ala Leu Val Gly Phe Glu Ile Ser Asn Asp Ser
        355                 360                 365

Met Thr Val Leu Lys Val Tyr Glu Ala Lys Leu Lys Gln Asn Tyr Gln
    370                 375                 380

Val Asp Lys Asp Ser Leu Ser Glu Val Ile Tyr Gly Asp Met Asp Lys
385                 390                 395                 400

Leu Leu Cys Pro Asp Gln Ser Glu Lys Ile Tyr Tyr Thr Asn Asn Ile
                405                 410                 415

Val Phe Pro Asn Glu Tyr Val Ile Thr Lys Ile Asp Phe Thr Lys Lys
            420                 425                 430

Met Lys Thr Leu Arg Tyr Glu Val Thr Ala Asn Ser Tyr Asp Ser Ser
        435                 440                 445

Thr Gly Glu Ile Asp Leu Asn Lys Lys Lys Val Glu Ser Ser Lys Ala

Glu Tyr Arg Thr Leu Ser Ala Asn Asn Asp Gly Val Tyr Met Pro Leu
465                 470                 475                 480

Gly Val Ile Ser Glu Thr Phe Leu Thr Pro Ile Asn Gly Phe Gly Leu
                485                 490                 495

Gln Ala Asp Glu Asn Ser Arg Leu Ile Thr Leu Thr Cys Lys Ser Tyr
            500                 505                 510

Leu Arg Glu Leu Leu Ala Thr Asp Leu Ser Asn Lys Glu Thr Lys
        515                 520                 525

Leu Ile Val Pro Pro Asn Ser Phe Ile Ser Asn Ile Val Glu Asn Gly
    530                 535                 540

Ser Ile Glu Glu Gly His Leu Glu Pro Trp Lys Ala Asn Asn Lys Asn
545                 550                 555                 560

Ala Tyr Val Asp His Thr Gly Gly Val Asn Gly Thr Lys Ala Leu Tyr
                565                 570                 575

Val His Glu Asp Gly Gly Val Ser Gln Phe Met Gly Asp Lys Leu Lys
            580                 585                 590

Pro Lys Thr Glu Tyr Val Ile Gln Tyr Thr Val Lys Gly Lys Pro Ser
        595                 600                 605

Ile His Leu Lys Asp Glu Asn Thr Gly Tyr Ile Leu Tyr Glu Asp Thr
    610                 615                 620

Asn Asn Asp Leu Glu Asp Phe Gln Thr Ile Thr Lys Arg Phe Thr Thr
625                 630                 635                 640

Gly Thr Asp Leu Met Arg Val Tyr Leu Ile Leu Lys Ser Gln Ser Gly
                645                 650                 655

His Glu Ala Trp Gly Asp Asn Phe Thr Ile Leu Glu Ile Lys Pro Ala
            660                 665                 670

Glu Ala Leu Val Ser Pro Glu Leu Ile Asn Pro Asn Ser Trp Ile Thr
        675                 680                 685

Thr Gln Gly Ala Ser Ile Ser Gly Asp Lys Leu Phe Ile Ser Leu Gly
    690                 695                 700

Thr Asn Gly Thr Phe Arg Gln Asn Leu Ser Leu Asn Ser Tyr Ser Thr
705                 710                 715                 720

Tyr Ser Ile Ser Phe Thr Ala Ser Gly Pro Phe Asn Val Thr Val Arg
                725                 730                 735

Asn Ser Arg Glu Val Leu Tyr Glu Arg Asn Asn Leu Met Ser Ser Thr
            740                 745                 750

Ser His Ile Ser Gly Glu Phe Lys Thr Glu Ser Asn Asn Thr Gly Leu
        755                 760                 765

Tyr Val Glu Leu Ser Arg Arg Ser Gly Gly Ala Gly His Ile Ser Phe
    770                 775                 780

Glu Asn Ile Ser Ile Lys
785                 790

<210> SEQ ID NO 15
<211> LENGTH: 2409
<212> TYPE: DNA
<213> ORGANISM: Artificial Sequence
<220> FEATURE:
<223> OTHER INFORMATION: synthetic sequence encoding AXMI-115

<400> SEQUENCE: 15
atgaacatga acaacaccaa gctcaatgca agagctcttc cttccttcat cgactacttc      60
aatggcatct atggcttcgc caccggcatc aaggacatca tgaacatgat cttcaagaca     120
gacactggag gagatctcac cttggatgag atcctcaaga accagcagct gctgaatgag     180

```
atctcaggga agctggatgg cgtcaatgga agcctcaatg atctcattgc tcaaggaaac    240
ctcaacacag agctctccaa ggagatcctc aagatcgcca atgagcagaa ccaggtgctg    300
aatgatgtca acaacaagct ggatgccatc aacaccatgc tgaacatcta cctccccaag    360
atcacctcaa tgctctctga tgtgatgaag cagaactatg ctctctccct ccagatcgag    420
tacctctcaa ggcagctgca agagatctcc gacaagctgg atgtcatcaa cctcaatgtg    480
ctgatcaaca gcaccttgac agagatcacc ccaagctacc agaggatcaa atatgtcaat    540
gagaagttcg acaagctcac cttcgccaca gaatcaaccc tccgcgccaa gcaaggcatc    600
ttcaatgagg acagcttcga caacaacacc ttggagaact tgacagatct tgctgagctg    660
gccaagagca tcaccaagaa tgatgtggac agcttcgagt tctacctcca caccttccat    720
gatgtgctga ttggcaacaa cctctttgga agaagcgcgc tcaagacagc ttcagagctc    780
atcaccaagg atgagatcaa gacatctgga tcagagattg gcaaggtgta cagcttcctc    840
atcgtcctca ccagcctcca ggccaaggcc ttcctcaccc tcaccacctg ccggaagctg    900
ctgggcctct ccgacatcga ctacacctcc atcatgaatg agcacctcaa caatgagaag    960
aatgagttca gagacaacat cctgccggcg ctctccaaca agttcagcaa cccttcatat   1020
gcaaaaacca tcggcagcga caactacgcc aaggtgatcc tggagagcga gcctggatat   1080
gctctggtgg gcttcgagat catcaatgat cccatccccg tgctgaaggc ctacaaggcc   1140
aagctgaagc agaactacca ggtggacaac cagagcctct cagagatcgt ctacctggac   1200
atcgacaagc tcttctgccc agagaacagc gagcagaagt actacaccaa gaacctcacc   1260
ttccctgatg gatatgtcat caccaagatc accttcgaga agaagctcaa caacctcatc   1320
tatgaagcca ccgccaactt ctatgatcca tcaactggag acatcgacct gaacaagaag   1380
caggtggaga gcaccttccc tcaaacagac tacatcacca tggacattgg agatgatgat   1440
ggcatctaca tgccgctcgg cgtcatctca gaaaccttcc tcaccccat caacagcttc    1500
ggcctggagg tggatgccaa gagcaagacc ctcaccttga aatgcaagag ctacctcagg   1560
gagtacctgc tggagagtga tctgaagaac aaggaaacag gctgatcgc gccgccaaat    1620
gttttcatca gcaatgtggt gaagaactgg acattgaag aagattcatt ggagccatgg    1680
gtggccaaca acaagaatgc ttatgtggac aacaccggcg gcattgaaag aagcaaggcg   1740
ctcttcaccc aaggagatgg agagttctca cagttcatcg gcgacaagct gaagccaaac   1800
accgactaca tcatccagta caccgtcaag ggcaagccgg ccatctacct caagaacaag   1860
agcaccggct acatcacata tgaggacacc aatggcaaca gcgaggagtt ccaaaccatt   1920
gctgtgaagt tcacctcaga aacagatctc tcccaaaccc acctggtgtt caagagccaa   1980
aatggatatg aagcatgggg agacaacttc atcatcctgg aggccaagct ctttgaaaca   2040
ccagaatctc cagagctcat caagttcaat gattgggaga gatttggcac acctacatc    2100
actggaaatg agctgaggat tgatcattca agaggaggct acttccgcca gagcttgaac   2160
atcgacagct acagcacata tgatctctcc ttctccttct ccggcctctg ggccaaggtc   2220
atcgtcaaga acagcagagg agtggtgctc ttcgagaagg tgaagaacaa tggaagcagc   2280
tatgaggaca tctcagagag cttcaccacc gccagcaaca aggatggctt cttcatcgag   2340
ctcaccgccg agaggacaag cagcaccttc cacagcttca gagacatctc catcaaggag   2400
aagatcgag                                                            2409
```

<210> SEQ ID NO 16
<211> LENGTH: 2409

<212> TYPE: DNA
<213> ORGANISM: Artificial Sequence
<220> FEATURE:
<223> OTHER INFORMATION: synthetic sequence encoding AXMI-115

<400> SEQUENCE: 16

| | | | | | |
|---|---|---|---|---|---|
| atgaacatga | acaacaccaa | gctcaatgca | agagctcttc | cttccttcat cgactacttc | 60 |
| aatggcatct | atggcttcgc | caccggcatc | aaggacatca | tgaacatgat cttcaagaca | 120 |
| gacactggag | agatctcac | cttggatgag | atcctcaaga | accagcagct gctgaatgag | 180 |
| atctcaggga | agctggatgg | cgtcaatgga | agcctcaatg | atctcattgc tcaaggaaac | 240 |
| ctcaacacag | agctctccaa | ggagatcctc | aagattgcaa | atgagcagaa ccaggtgctg | 300 |
| aatgatgtca | caacaagct | ggatgccatc | aacaccatgc | tgaacatcta cctccccaag | 360 |
| atcacctcaa | tgctctctga | tgtgatgaag | cagaactatg | ctctctccct ccagatcgag | 420 |
| tacctctcaa | ggcagctgca | agagatctcc | gacaagctgg | atgtcatcaa cctcaatgtg | 480 |
| ctgatcaaca | gcaccttgac | agagatcacc | ccaagctacc | aaaggatcaa atatgtcaat | 540 |
| gagaagttcg | acaagctcac | cttcgccaca | gaatcaaccc | tccgcgccaa gcaaggcatc | 600 |
| ttcaatgagg | acagcttcga | caacaacacc | ttggagaact | gacagatct tgctgagctg | 660 |
| gccaagagca | tcaccaagaa | tgatgtggac | agcttcgagt | ctacctcca caccttccat | 720 |
| gatgtgctga | ttggcaacaa | cctctttgga | agaagcgcgc | tcaagacagc ttcagagctc | 780 |
| atcaccaagg | atgagatcaa | gacatctgga | tcagaaattg | gcaaggtgta cagcttcctc | 840 |
| atcgtcctca | ccagcctcca | ggccaaggcc | ttcctcaccc | tcaccacctg ccggaagctg | 900 |
| ctgggcctct | ccgacatcga | ctacaccctcc | atcatgaatg | agcacctcaa caatgagaag | 960 |
| aatgagttca | gagacaacat | cctgccggcg | ctctccaaca | agttcagcaa cccttcatat | 1020 |
| gcaaaaacca | tcggcagcga | caactatgcc | aaggtgatcc | tggagagcga gcctggatat | 1080 |
| gctctggtgg | gcttcgagat | catcaatgat | cccatccctg | tgctgaaggc ctacaaggcc | 1140 |
| aagctgaagc | agaactacca | ggtggacaac | caaagcctct | cagagatcgt ctacctggac | 1200 |
| atcgacaagc | tcttctgccc | agagaacagc | gagcagaagt | actacaccaa gaacctcacc | 1260 |
| ttccctgatg | gatatgtcat | caccaagatc | accttcgaga | agaagctcaa caacctcatc | 1320 |
| tatgaagcca | ccgccaactt | ctatgatcca | tcaactggag | acattgatct gaacaagaag | 1380 |
| caggtggaga | gcaccttccc | tcaaacagat | tacatcacca | tggacattgg agatgatgat | 1440 |
| ggcatctaca | tgccgctcgg | cgtcatctca | gaaaccttcc | tcaccccat caacagcttc | 1500 |
| ggcctggagg | tggatgccaa | gagcaagacc | ctcaccttga | aatgcaagag ctacttgagg | 1560 |
| gagtacctgc | tggaatcaga | tctgaagaac | aaggaaacag | gctgatcgc gccgccaaat | 1620 |
| gttttcatca | gcaatgtggt | gaagaactgg | gacattgaag | aagattcatt ggagccatgg | 1680 |
| gtggccaaca | acaagaatgc | ttatgtggac | aacaccggcg | gcattgaaag aagcaaggcg | 1740 |
| ctcttcaccc | aaggagatgg | agagttctca | cagttcatcg | cgacaagct gaagccaaac | 1800 |
| accgactaca | tcatccagta | caccgtcaag | ggcaagccgg | ccatctacct caagaacaag | 1860 |
| agcactggct | acatcacata | tgaggacacc | aatggcaaca | cgaggagtt ccaaacaatt | 1920 |
| gctgtgaagt | tcacctcaga | aacagatctc | tcccaaaccc | acctggtgtt caagagccaa | 1980 |
| aatggatatg | aagcatgggg | agacaacttc | atcatcctgg | aggccaagct ctttgaaaca | 2040 |
| ccagaatctc | cagagctcat | caagttcaat | gattgggaaa | gatttggcac cacctacatc | 2100 |
| actgaaaatg | agctgaggat | tgatcattca | agaggaggct | acttccgcca gagcttgaac | 2160 |
| atcgacagct | acagcacata | tgatctctcc | ttctccttct | ccggcctctg ggccaaggtc | 2220 |

| | |
|---|---|
| atcgtcaaga acagcagagg agtggtgctc ttcgagaagg tgaagaacaa tggaagcagc | 2280 |
| tatgaggaca tctcagagag cttcaccacc gccagcaaca aggatggctt cttcatcgag | 2340 |
| ctcaccgccg agaggacaag cagcaccttc cacagcttca gagacatctc catcaaggag | 2400 |
| aagattgaa | 2409 |

<210> SEQ ID NO 17
<211> LENGTH: 2364
<212> TYPE: DNA
<213> ORGANISM: Artificial Sequence
<220> FEATURE:
<223> OTHER INFORMATION: synthetic sequence encoding AXMI-184

<400> SEQUENCE: 17

| | |
|---|---|
| atgaacaaga caacaccaa gctctccgcg cgcgcgctgc cctccttcat cgactacttc | 60 |
| aatggcatct atggcttcgc caccggcatc aaggacatca tgaacatgat cttcaagaca | 120 |
| gacactggag agatctcac cttggatgag atcctcaaga ccagcagct gctgaatgac | 180 |
| atctcaggga agctggatgg cgtcaatgga agcctcaatg atctcattgc tcaaggaaac | 240 |
| ctcaacacag agctctccaa ggagatcctc aagatcgcca tgagcagaa ccaggtgctg | 300 |
| aatgatgtca caacaagct ggatgccatc aacaccatgc tgcatgtcta cctcccccaag | 360 |
| atcacctcaa tgctctctga tgtgatgaag ccaaactatg ctctctccat gcaaattgag | 420 |
| tacctctcaa ggcagctgca agagatctcc gacaagctgg acatcatcaa tgtcaatgtg | 480 |
| ctgatcaaca gcaccttgac agagatcacg ccggcctacc aatggatcaa atatgtcaat | 540 |
| gagaagtttg aggagctcac cttcgccaca gaaacaacct tgaaggtgaa gaatgattca | 600 |
| gcttctgctg acatcctgga tgagctgaca gagctgacag agctggccaa gagcgtcacc | 660 |
| aagaatgatg ttgatggctt cgagttctac ctcaacacct tccatgatgt gatggtgggc | 720 |
| aacaacctct ttggaagaag caccctcaag acagcttcag agctgatcgc caaggagaat | 780 |
| gtcaagacat ctggaagcga ggtgggaaat gtctacaact tcctggtggt gctgacggcg | 840 |
| ctgcaagcaa aggccttcct caccctcacc acctgccgga agctgctggg cctcgccgac | 900 |
| atcgactaca cctcaatcat gaatgagcac ctcaacaagg agaaggagga gttcagagtg | 960 |
| aacatcctcc ccatcctctc caacaccttc agcaacccca actacgccaa ggtgaagggc | 1020 |
| tcagatgaag atgccaagat gattgtggag gccaagcctg ccatgctct ggtgggcttc | 1080 |
| gagatcagca tgacagcat gacggtgctg aaggtgtatg aagcaaagct gaagcagaac | 1140 |
| taccaggtgg acaaggacag cctctccgag gtgatctatg agacatgga caagctgctc | 1200 |
| tgcccagatc aatcagagaa gatctactac accaacaaca tcgtctttcc aaatgaatat | 1260 |
| gtcatcacca agatcgactt caccaagaag atgaaaacct tgagatatga agtcaccgcc | 1320 |
| aacagctatg attcttcaac tggagagatc gacctcaaca agaagaaggt ggagagcagc | 1380 |
| aaggcagagt acaggacgct ctccgccaac aatgatggcg tctacatgcc gctcggcgtc | 1440 |
| atctcagaaa ccttcttgac gcccatcaat ggcttcggcc tccaagctga tgagaacagc | 1500 |
| aggctcatca ccctcacctg caagagctac ctcagggagc tgctgctggc caccgacctc | 1560 |
| tccaacaagg aaacaaagct gattgttcct ccaaacagct tcatcagcaa catcgtggag | 1620 |
| aatggaagca ttgaagaagg ccacctagag ccatggaagg ccaacaacaa gaatgcatat | 1680 |
| gtggaccaca ccggcggcgt caatggcacc aaggcgctct atgttcatga agatggagga | 1740 |
| gttcacagt tcatgggaga caagctgaag ccaaaaacag aatatgtcat ccagtacacc | 1800 |
| gtcaagggca agccaagcat ccacctcaag gatgagaaca ccggctacat cctctacgag | 1860 |

```
gacaccaaca atgatttaga agatttccaa accatcacca agaggttcac cactggaaca    1920
gatctgatga gggtgtacct catcctcaag agccaaagtg gtcatgaagc atggggagac    1980
aacttcacca tcctggagat caagccagca gaagctctgg tgtcgccgga gctcatcaac    2040
cccaacagct ggataacaac acaaggagct tcaatttctg gtgacaagct cttcatctcc    2100
cttggaacaa atggcacctt ccgccagaac ctctccctca acagctacag cacctacagc    2160
atcagcttca ccgcctcagg ccccttcaat gtcaccgtca ggaacagcag ggaggtgctg    2220
tatgaaagga caacttgat gagcagcacc agccacatct ctggagagtt caagacagaa     2280
agcaacaaca ccggcctcta tgtggagctc tcaagaagaa gcggcggcgc cggccacatc    2340
agcttcgaga acatctccat caag                                           2364
```

```
<210> SEQ ID NO 18
<211> LENGTH: 2364
<212> TYPE: DNA
<213> ORGANISM: Artificial Sequence
<220> FEATURE:
<223> OTHER INFORMATION: synthetic sequence encoding AXMI-184

<400> SEQUENCE: 18
```

```
atgaacaaga caacaccaa gctctccgcg cgcgcgctgc catccttcat cgactacttc     60
aatggcatct atggcttcgc caccggcatc aaggacatca tgaacatgat cttcaagaca    120
gacactggag gagatctcac cttggatgag atcctcaaga accagcagct gctgaatgac    180
atctcaggga gctggatgg cgtcaatgga agcctcaatg atctcattgc tcaaggaaac    240
ctcaacacag agctctccaa ggagatcctc aagattgcaa atgagcagaa ccaggtgctg    300
aatgatgtca caacaagct ggatgccatc aacaccatgc tgcatgtcta cctccccaag    360
atcacctcaa tgctctctga tgtgatgaag ccaaattatg ctctctccat gcaaattgag    420
tacctctcaa ggcagctgca agagatctcc gacaagctgg acatcatcaa tgtcaatgtt    480
ctcatcaaca gcaccttgac agagatcacg ccggcctacc aatggatcaa atatgtcaat    540
gagaagtttg aggagctcac cttcgccaca gaaacaacat tgaaggtgaa gaatgattca    600
gcttctgctg acatcctgga tgagctgaca gagctgacag agctggccaa gagcgtcacc    660
aagaatgatg ttgatggctt cgagttctac ctcaacaccct tccatgatgt gatggtgggc    720
aacaacctct ttggaagaag cacctcaag acagcttcag agctgatcgc caaggaaaat    780
gtcaagacat ctggatcaga ggttggaaat gtctacaact tcttggtggt gctgacggcg    840
ctgcaagcaa aggccttcct caccctcacc acctgccgga gctgctggg cctcgccgac    900 atcgactaca cctcaatcat gaatgagcac ctcaacaagg agaaggagga gttcagagtg    960
aacatcctcc ccatcctctc caacaccttc agcaaccca actatgccaa ggtgaagggc    1020
tcagatgaag atgccaagat gattgtggag gccaagcctg ccatgctct ggtgggcttc    1080 gagatcagca atgacagcat gacagtgctg aaggtttatg aagcaaagct gaagcagaac    1140
taccaggtgg acaaggacag cctctcagag gtgatctatg agacatgga caagctgctc    1200 tgcccagatc aatcagagaa gatctactac accaacaaca tcgtctttcc aaatgaatat    1260
gtcatcacca gatcgactt caccaagaag atgaaacat tgagatatga agtcaccgcc    1320
aacagctatg attcttcaac tggagagatc gacctcaaca agaagaaggt ggagagcagc    1380
aaggcagagt acaggacgct ctccgccaac aatgatggcg tctacatgcc gctcggcgtc    1440
atctcagaaa ccttccttgac gcccatcaat ggcttcggcc tccaagctga tgaaaacagc    1500
aggctcatca ccctcacctg caagagctac ttgagggagc tgctgctggc caccgacctc    1560
```

```
tccaacaagg aaacaaagct gattgttcct ccaaacagct tcatcagcaa cattgtggag    1620
aatggaagca ttgaagaagg ccacctagag ccatggaagg ccaacaacaa gaatgcatat    1680
gttgatcaca ccggcggcgt caatggcacc aaggcgctct atgttcatga agatggagga    1740
gtttcacagt tcatgggaga caagctgaag ccaaaaacag aatatgtcat ccagtacacc    1800
gtcaagggca agccaagcat ccacctcaag gatgaaaaca ctggctacat cctctatgag    1860
gacaccaaca atgatttaga agattttcaa accatcacca agaggttcac cactggaaca    1920
gatctgatga gggtgtacct catcctcaag agccaaagtg gtcatgaagc atggggagac    1980
aacttcacca tcctggagat caagccagca gaagctctgg tgtcgccgga gctcatcaac    2040
cccaacagct ggataacaac acaaggagct tcaatttctg gtgacaagct cttcatctcc    2100
cttggaacaa atggcacctt ccgccagaac ctctccctca cagctacag cacctacagc     2160 atcagcttca ccgcctcagg acccttcaat gtcaccgtca ggaacagcag ggaggtgctg    2220
tatgaaagga caacttgat  gagcagcacc agccacatct ctggagagtt caagacagaa    2280
agcaacaaca ccggcctcta tgtggagctc tcaagaagaa gcggcggcgc cggccacatc    2340
agcttcgaga acatctccat caag                                           2364
```

<210> SEQ ID NO 19
<211> LENGTH: 4
<212> TYPE: PRT
<213> ORGANISM: Artificial Sequence
<220> FEATURE:
<223> OTHER INFORMATION: endoplasmic reticulum targeting peptide

<400> SEQUENCE: 19

Lys Asp Glu Leu
 1

<210> SEQ ID NO 20
<211> LENGTH: 41
<212> TYPE: DNA
<213> ORGANISM: Artificial Sequence
<220> FEATURE:
<223> OTHER INFORMATION: oligonucleotide primer for domain swapping

<400> SEQUENCE: 20
aacaccggcg gcgtcaatgg aacaagggcg ctcttcaccc a                         41

<210> SEQ ID NO 21
<211> LENGTH: 41
<212> TYPE: DNA
<213> ORGANISM: Artificial Sequence
<220> FEATURE:
<223> OTHER INFORMATION: oligonucleotide primer for domain swapping

<400> SEQUENCE: 21
tgggtgaaga gcgcccttgt tccattgacg ccgccggtgt t                         41

<210> SEQ ID NO 22
<211> LENGTH: 55
<212> TYPE: DNA
<213> ORGANISM: Artificial Sequence
<220> FEATURE:
<223> OTHER INFORMATION: oligonucleotide primer for domain swapping

<400> SEQUENCE: 22
gcccggagct catcaatgtc aacaactgga tcagaactgg caccacctac atcac          55

<210> SEQ ID NO 23

```
<211> LENGTH: 55
<212> TYPE: DNA
<213> ORGANISM: Artificial Sequence
<220> FEATURE:
<223> OTHER INFORMATION: oligonucleotide primer for domain swapping

<400> SEQUENCE: 23
gtgatgtagg tggtgccagt tctgatccag ttgttgacat tgatgagctc cgggc         55

<210> SEQ ID NO 24
<211> LENGTH: 50
<212> TYPE: DNA
<213> ORGANISM: Artificial Sequence
<220> FEATURE:
<223> OTHER INFORMATION: oligonucleotide primer for domain swapping

<400> SEQUENCE: 24
atgattggga gaggttcgga agcacccaca tcagcggcaa tgagctgagg              50

<210> SEQ ID NO 25
<211> LENGTH: 50
<212> TYPE: DNA
<213> ORGANISM: Artificial Sequence
<220> FEATURE:
<223> OTHER INFORMATION: oligonucleotide primer for domain swapping

<400> SEQUENCE: 25
cctcagctca ttgccgctga tgtgggtgct tccgaacctc tcccaatcat              50

<210> SEQ ID NO 26
<211> LENGTH: 55
<212> TYPE: DNA
<213> ORGANISM: Artificial Sequence
<220> FEATURE:
<223> OTHER INFORMATION: oligonucleotide primer for domain swapping

<400> SEQUENCE: 26
ctacatcacc ggcaatacct tgacgctcta ccaaggagga ggaggctact tccgc         55

<210> SEQ ID NO 27
<211> LENGTH: 55
<212> TYPE: DNA
<213> ORGANISM: Artificial Sequence
<220> FEATURE:
<223> OTHER INFORMATION: oligonucleotide primer for domain swapping

<400> SEQUENCE: 27
gcggaagtag cctcctcctc cttggtagag cgtcaaggta ttgccggtga tgtag         55

<210> SEQ ID NO 28
<211> LENGTH: 57
<212> TYPE: DNA
<213> ORGANISM: Artificial Sequence
<220> FEATURE:
<223> OTHER INFORMATION: oligonucleotide primer for domain swapping

<400> SEQUENCE: 28
cgacagctac agcacctaca gggtgaactt ctccgtcacc ggctgggcca aggtgat       57

<210> SEQ ID NO 29
<211> LENGTH: 57
<212> TYPE: DNA
<213> ORGANISM: Artificial Sequence
<220> FEATURE:
<223> OTHER INFORMATION: oligonucleotide primer for domain swapping

<400> SEQUENCE: 29
```

```
atcaccttgg cccagccggt gacggagaag ttcaccctgt aggtgctgta gctgtcg         57
```

<210> SEQ ID NO 30
<211> LENGTH: 47
<212> TYPE: DNA
<213> ORGANISM: Artificial Sequence
<220> FEATURE:
<223> OTHER INFORMATION: oligonucleotide primer for domain swapping

<400> SEQUENCE: 30

```
gcttcagcgg cctcgacgcc aatgtgagga tcagaaacag ccgcggc                    47
```

<210> SEQ ID NO 31
<211> LENGTH: 47
<212> TYPE: DNA
<213> ORGANISM: Artificial Sequence
<220> FEATURE:
<223> OTHER INFORMATION: oligonucleotide primer for domain swapping

<400> SEQUENCE: 31

```
gccgcggctg tttctgatcc tcacattggc gtcgaggccg ctgaagc                    47
```

<210> SEQ ID NO 32
<211> LENGTH: 59
<212> TYPE: DNA
<213> ORGANISM: Artificial Sequence
<220> FEATURE:
<223> OTHER INFORMATION: oligonucleotide primer for domain swapping

<400> SEQUENCE: 32

```
gtgaagaaca gccgcgaggt gctcttcgag aagagataca tgaatggaag cagctatga      59
```

<210> SEQ ID NO 33
<211> LENGTH: 59
<212> TYPE: DNA
<213> ORGANISM: Artificial Sequence
<220> FEATURE:
<223> OTHER INFORMATION: oligonucleotide primer for domain swapping

<400> SEQUENCE: 33

```
tcatagctgc ttccattcat gtatctcttc tcgaagagca cctcgcggct gttcttcac      59
```

<210> SEQ ID NO 34
<211> LENGTH: 54
<212> TYPE: DNA
<213> ORGANISM: Artificial Sequence
<220> FEATURE:
<223> OTHER INFORMATION: oligonucleotide primer for domain swapping

<400> SEQUENCE: 34

```
ttcgagaagg tgaagaacag cggcgccaag gatgtttcag agagcttcac cacc            54
```

<210> SEQ ID NO 35
<211> LENGTH: 54
<212> TYPE: DNA
<213> ORGANISM: Artificial Sequence
<220> FEATURE:
<223> OTHER INFORMATION: oligonucleotide primer for domain swapping

<400> SEQUENCE: 35

```
ggtggtgaag ctctctgaaa catccttggc gccgctgttc ttcaccttct cgaa            54
```

<210> SEQ ID NO 36
<211> LENGTH: 53
<212> TYPE: DNA
<213> ORGANISM: Artificial Sequence
<220> FEATURE:

<223> OTHER INFORMATION: oligonucleotide primer for domain swapping

<400> SEQUENCE: 36
gcttcttcat cgagctcagc caaggcaaca acctctatag cagcaccttc cac       53

<210> SEQ ID NO 37
<211> LENGTH: 53
<212> TYPE: DNA
<213> ORGANISM: Artificial Sequence
<220> FEATURE:
<223> OTHER INFORMATION: oligonucleotide primer for domain swapping

<400> SEQUENCE: 37
gtggaaggtg ctgctataga ggttgttgcc ttggctgagc tcgatgaaga agc       53

<210> SEQ ID NO 38
<211> LENGTH: 51
<212> TYPE: DNA
<213> ORGANISM: Artificial Sequence
<220> FEATURE:
<223> OTHER INFORMATION: oligonucleotide primer for domain swapping

<400> SEQUENCE: 38
gaagcaaggc gctctatgtt cacaaggatg gaggcttcag ccagttcatc g         51

<210> SEQ ID NO 39
<211> LENGTH: 51
<212> TYPE: DNA
<213> ORGANISM: Artificial Sequence
<220> FEATURE:
<223> OTHER INFORMATION: oligonucleotide primer for domain swapping

<400> SEQUENCE: 39
cgatgaactg gctgaagcct ccatccttgt gaacatagag cgccttgctt c         51

<210> SEQ ID NO 40
<211> LENGTH: 50
<212> TYPE: DNA
<213> ORGANISM: Artificial Sequence
<220> FEATURE:
<223> OTHER INFORMATION: oligonucleotide primer for domain swapping

<400> SEQUENCE: 40
ccgccgagag gacaggaggg ccgctggtga agttcagaga catcagcatc           50

<210> SEQ ID NO 41
<211> LENGTH: 50
<212> TYPE: DNA
<213> ORGANISM: Artificial Sequence
<220> FEATURE:
<223> OTHER INFORMATION: oligonucleotide primer for domain swapping

<400> SEQUENCE: 41
gatgctgatg tctctgaact tcaccagcgg ccctcctgtc ctctcggcgg           50

<210> SEQ ID NO 42
<211> LENGTH: 48
<212> TYPE: DNA
<213> ORGANISM: Artificial Sequence
<220> FEATURE:
<223> OTHER INFORMATION: oligonucleotide primer for domain swapping

<400> SEQUENCE: 42
agcaccttcc acagcttcaa tgatgtgagc atcaagtaag gcgcgccg             48

<210> SEQ ID NO 43

```
<211> LENGTH: 48
<212> TYPE: DNA
<213> ORGANISM: Artificial Sequence
<220> FEATURE:
<223> OTHER INFORMATION: oligonucleotide primer for domain swapping

<400> SEQUENCE: 43
cggcgcgcct tacttgatgc tcacatcatt gaagctgtgg aaggtgct                    48

<210> SEQ ID NO 44
<211> LENGTH: 49
<212> TYPE: DNA
<213> ORGANISM: Artificial Sequence
<220> FEATURE:
<223> OTHER INFORMATION: oligonucleotide primer for domain swapping

<400> SEQUENCE: 44
cgacaagcta aagcccaaga cagaatatgt catccagtac accgtcaag                   49

<210> SEQ ID NO 45
<211> LENGTH: 49
<212> TYPE: DNA
<213> ORGANISM: Artificial Sequence
<220> FEATURE:
<223> OTHER INFORMATION: oligonucleotide primer for domain swapping

<400> SEQUENCE: 45
cttgacggtg tactggatga catattctgt ctttgggctttt agcttgtcg                 49

<210> SEQ ID NO 46
<211> LENGTH: 56
<212> TYPE: DNA
<213> ORGANISM: Artificial Sequence
<220> FEATURE:
<223> OTHER INFORMATION: oligonucleotide primer for domain swapping

<400> SEQUENCE: 46
cctacgagga caccaataac aacaacctgg aggactacca acaattgct gtgaag            56

<210> SEQ ID NO 47
<211> LENGTH: 56
<212> TYPE: DNA
<213> ORGANISM: Artificial Sequence
<220> FEATURE:
<223> OTHER INFORMATION: oligonucleotide primer for domain swapping

<400> SEQUENCE: 47
cttcacagca attgtttggt agtcctccag gttgttgtta ttggtgtcct cgtagg           56

<210> SEQ ID NO 48
<211> LENGTH: 57
<212> TYPE: DNA
<213> ORGANISM: Artificial Sequence
<220> FEATURE:
<223> OTHER INFORMATION: oligonucleotide primer for domain swapping

<400> SEQUENCE: 48
gaggagttcc aaacaattac caagaggttc accaccggca cagatttgag ccagacc          57

<210> SEQ ID NO 49
<211> LENGTH: 57
<212> TYPE: DNA
<213> ORGANISM: Artificial Sequence
<220> FEATURE:
<223> OTHER INFORMATION: oligonucleotide primer for domain swapping

<400> SEQUENCE: 49
```

```
ggtctggctc aaatctgtgc cggtggtgaa cctcttggta attgtttgga actcctc        57
```

<210> SEQ ID NO 50
<211> LENGTH: 58
<212> TYPE: DNA
<213> ORGANISM: Artificial Sequence
<220> FEATURE:
<223> OTHER INFORMATION: oligonucleotide primer for domain swapping

<400> SEQUENCE: 50

```
cacctcagaa acagatttga agggcgtcta cctcatcttg aagagccaaa atggatat     58
```

<210> SEQ ID NO 51
<211> LENGTH: 58
<212> TYPE: DNA
<213> ORGANISM: Artificial Sequence
<220> FEATURE:
<223> OTHER INFORMATION: oligonucleotide primer for domain swapping

<400> SEQUENCE: 51

```
atatccattt tggctcttca agatgaggta gacgcccttc aaatctgttt ctgaggtg     58
```

<210> SEQ ID NO 52
<211> LENGTH: 45
<212> TYPE: DNA
<213> ORGANISM: Artificial Sequence
<220> FEATURE:
<223> OTHER INFORMATION: oligonucleotide primer for domain swapping

<400> SEQUENCE: 52

```
tcctggaggc caagccatca gagaagctgc tcagcccgga gctca                   45
```

<210> SEQ ID NO 53
<211> LENGTH: 45
<212> TYPE: DNA
<213> ORGANISM: Artificial Sequence
<220> FEATURE:
<223> OTHER INFORMATION: oligonucleotide primer for domain swapping

<400> SEQUENCE: 53

```
tgagctccgg gctgagcagc ttctctgatg gcttggcctc cagga                   45
```

<210> SEQ ID NO 54
<211> LENGTH: 67
<212> TYPE: DNA
<213> ORGANISM: Artificial Sequence
<220> FEATURE:
<223> OTHER INFORMATION: oligonucleotide primer for domain swapping

<400> SEQUENCE: 54

```
atcattcaag aggaggcaac ctcaagcaga acctccagct tgacagcttc agcacctacg    60
acctcag                                                              67
```

<210> SEQ ID NO 55
<211> LENGTH: 67
<212> TYPE: DNA
<213> ORGANISM: Artificial Sequence
<220> FEATURE:
<223> OTHER INFORMATION: oligonucleotide primer for domain swapping

<400> SEQUENCE: 55

```
ctgaggtcgt aggtgctgaa gctgtcaagc tggaggttct gcttgaggtt gcctcctctt    60
gaatgat                                                              67
```

<210> SEQ ID NO 56

```
<211> LENGTH: 70
<212> TYPE: DNA
<213> ORGANISM: Artificial Sequence
<220> FEATURE:
<223> OTHER INFORMATION: oligonucleotide primer for domain swapping

<400> SEQUENCE: 56
gctatgagga catctcagag atcttcacca ccaagctggg caaggacaac ttctacatcg    60
agctcaccgc                                                          70

<210> SEQ ID NO 57
<211> LENGTH: 70
<212> TYPE: DNA
<213> ORGANISM: Artificial Sequence
<220> FEATURE:
<223> OTHER INFORMATION: oligonucleotide primer for domain swapping

<400> SEQUENCE: 57
gcggtgagct cgatgtagaa gttgtccttg cccagcttgg tggtgaagat ctctgagatg    60
tcctcatagc                                                          70

<210> SEQ ID NO 58
<211> LENGTH: 69
<212> TYPE: DNA
<213> ORGANISM: Artificial Sequence
<220> FEATURE:
<223> OTHER INFORMATION: oligonucleotide primer for domain swapping

<400> SEQUENCE: 58
caagggcaag ccgtcaatcc acctcaagaa tgagaacacc ggctacatcc actacgagga    60
caccaatgg                                                           69

<210> SEQ ID NO 59
<211> LENGTH: 69
<212> TYPE: DNA
<213> ORGANISM: Artificial Sequence
<220> FEATURE:
<223> OTHER INFORMATION: oligonucleotide primer for domain swapping

<400> SEQUENCE: 59
ccattggtgt cctcgtagtg gatgtagccg gtgttctcat tcttgaggtg gattgacggc    60
ttgcccttg                                                           69

<210> SEQ ID NO 60
<211> LENGTH: 76
<212> TYPE: DNA
<213> ORGANISM: Artificial Sequence
<220> FEATURE:
<223> OTHER INFORMATION: oligonucleotide primer for domain swapping

<400> SEQUENCE: 60
caagagccaa aatggagatg aagcatgggg agacaacttc accatcctgg agatctcgct    60
cttcgagaca ccagaa                                                   76

<210> SEQ ID NO 61
<211> LENGTH: 76
<212> TYPE: DNA
<213> ORGANISM: Artificial Sequence
<220> FEATURE:
<223> OTHER INFORMATION: oligonucleotide primer for domain swapping
```

-continued

<400> SEQUENCE: 61

```
ttctggtgtc tcgaagagcg agatctccag gatggtgaag ttgtctcccc atgcttcatc     60
tccattttgg ctcttg                                                     76
```

The invention claimed is:

1. An isolated or recombinant nucleic acid molecule comprising a nucleotide sequence selected from the group consisting of:

a) the nucleotide sequence of SEQ ID NO:3;

b) a nucleotide sequence that encodes a polypeptide comprising the amino acid sequence of SEQ ID NO:6; and c) a nucleotide sequence encoding an insecticidal polypeptide that is a variant of SEQ ID NO:6, wherein said variant is the result of one or more domain(s) of SEQ ID NO:4, 5, 13, or 14 being exchanged with the corresponding domain(s) of SEQ ID NO:6, wherein said nucleotide sequence encodes an insecticidal polypeptide.

2. The nucleic acid molecule of claim 1, wherein said nucleotide sequence is selected from the group consisting of SEQ ID NO:15 and 16.

3. An expression cassette comprising the nucleic acid molecule of claim 1.

4. The expression cassette of claim 3, further comprising a nucleic acid molecule encoding a heterologous polypeptide.

5. A host cell that contains the recombinant nucleic acid molecule of claim 1.

6. An isolated polypeptide with insecticidal activity, selected from the group consisting of:

a) a polypeptide comprising the amino acid sequence of SEQ ID NO:6;

b) a polypeptide that is encoded by the nucleotide sequence of any of SEQ ID NO:1, 2, 3, 11, or 12; and c) a polypeptide that is a variant of SEQ ID NO:6, wherein said variant is the result of one or more domain(s) of SEQ ID NO:4, 5, 13, or 14 being exchanged with the corresponding domain(s) of SEQ ID NO:6, wherein said polypeptide has insecticidal activity.

7. The polypeptide of claim 6 further comprising heterologous amino acid sequences.

8. A composition comprising the isolated or recombinant nucleic acid molecule according to claim 1.

9. The composition of claim 8, wherein said composition is selected from the group consisting of a powder, dust, pellet, granule, spray, emulsion, colloid, and solution.

10. The composition of claim 8, wherein said composition is prepared by desiccation, lyophilization, homogenization, extraction, filtration, centrifugation, sedimentation, or concentration of a culture of *Bacillus thuringiensis* cells.

11. A plant having stably incorporated into its genome a DNA construct comprising a nucleotide sequence that encodes a protein having insecticidal activity, wherein said nucleotide sequence is selected from the group consisting of:

a) a nucleotide sequence of SEQ ID NO:3; and b) a nucleotide sequence that encodes a polypeptide comprising the amino acid sequence of SEQ ID NO:6; and wherein said nucleotide sequence is operably linked to a promoter that drives expression of a coding sequence in a plant cell.

12. The plant of claim 11, wherein said plant is a plant cell.

13. A transgenic seed of the plant of claim 11.

14. The plant of claim 11, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

15. A method for protecting a plant from an insect pest, comprising introducing into said plant or cell thereof at least one expression vector comprising the nucleic acid molecule of claim 1.

16. The nucleic acid molecule of claim 1, wherein said nucleotide sequence is operably linked to a promoter capable of directing expression of said nucleotide sequence in a plant cell.

* * * * *